(12) United States Patent
Griessl et al.

(10) Patent No.: US 11,208,643 B2
(45) Date of Patent: Dec. 28, 2021

(54) ENGINEERED GRAM-NEGATIVE ENDOLYSINS

(71) Applicant: SASINAPAS CO., LTD., Bangkok (TH)

(72) Inventors: Martin Griessl, Hohenschambach (DE); Manfred Biebl, Obertraubling (DE)

(73) Assignee: SASINAPAS CO., LTD., Bangkok (TH)

( * ) Notice: Subject to any disclaimer, the term of this patent is extended or adjusted under 35 U.S.C. 154(b) by 0 days.

(21) Appl. No.: 16/500,163

(22) PCT Filed: Apr. 2, 2018

(86) PCT No.: PCT/IB2018/052253
§ 371 (c)(1),
(2) Date: Oct. 2, 2019

(87) PCT Pub. No.: WO2018/185634
PCT Pub. Date: Oct. 11, 2018

(65) Prior Publication Data
US 2021/0108185 A1 Apr. 15, 2021

(30) Foreign Application Priority Data

Apr. 3, 2017 (WO) .................. PCT/IB2017/051886

(51) Int. Cl.
*C12N 9/36* (2006.01)
*C07K 14/005* (2006.01)
*A61K 38/00* (2006.01)

(52) U.S. Cl.
CPC .......... *C12N 9/2462* (2013.01); *C07K 14/005* (2013.01); *A61K 38/00* (2013.01)

(58) Field of Classification Search
None
See application file for complete search history.

(56) References Cited

FOREIGN PATENT DOCUMENTS

WO    WO 2010/023207    3/2010

OTHER PUBLICATIONS

Briers, Yves, and Rob Lavigne. "Breaking barriers: expansion of the use of endolysins as novel antibacterials against Gram-negative bacteria." *Future Microbiology* 10.3 (2015): 377-390.
Briers, Yves, et al. "Engineered endolysin-based "Artilysins" to combat multi-drugresistant gram-negative pathogens." *MBio* 5.4 (2014): e01379-14.
Briers, Yves, et al. "The high-affinity peptidoglycan binding domain of Pseudomonas phage endolysin KZ144." *Biochemical and Biophysical Research Communications* 383.2 (2009): 187-191.
International Search Report and Written Opinion issued in International Application No. PCT/IB2018/052253, dated Aug. 3, 2018.
Nelson, Daniel C. et al., "Endolysins as antimicrobials," In: Advances in Virus Research, Chapter 7, vol. 82, (2012):pp. 299-365.
Schmelcher, Mathias, Vincent S. Tchang, and Martin J. Loessner. "Domain shuffling and module engineering of Listeria phage endolysins for enhanced lytic activity and binding affinity." *Microbial Biotechnology* 4.5 (2011): 651-662.
Young, Ryland. "Phage lysis: three steps, three choices, one outcome." *Journal of Microbiology* 52.3 (2014): 243-258.

*Primary Examiner* — Suzanne M Noakes
*Assistant Examiner* — Jae W Lee
(74) *Attorney, Agent, or Firm* — Parker Highlander PLLC

(57) ABSTRACT

The present invention relates in general to the field of antimicrobial enzymes. In particular, the present invention relates to a polypeptide comprising the amino acid sequence of a globular Gram-negative endolysin and the amino acid sequence of a cell wall binding domain of i) a modular Gram-negative endolysin or ii) a bacteriophage tail/baseplate protein. The present invention relates also to corresponding nucleic acids, vectors, bacteriophages, host cells, and compositions. The present inventions also relates to the use of the polypeptide, nucleic acids, vectors, bacteriophages, host cells, and compositions in methods for treatment of the human or animal body by surgery or therapy or in diagnostic methods practiced on the human or animal body. The polypeptides, nucleic acids, vectors, bacteriophages, host cells, and compositions according to the invention may also be used as an antimicrobial in, e.g., food or feed, in cosmetics, or as disinfecting agent.

16 Claims, 5 Drawing Sheets
Specification includes a Sequence Listing.

ENGINEERED GRAM-NEGATIVE ENDOLYSINS

This application is a national phase application under 35 U.S.C. § 371 of International Application No. PCT/IB2018/052253, filed Apr. 2, 2018, which claims benefit of priority to International Application No. PCT/IB2017/051886, filed Apr. 3, 2017, the entire contents of each of which are hereby incorporated by reference.

BACKGROUND OF THE INVENTION

I. Field of the Invention

The present invention relates to the field of antimicrobial enzymes. In particular, the present invention relates to a polypeptide comprising the amino acid sequence of a globular Gram-negative endolysin and the amino acid sequence of a cell wall binding domain of i) a modular Gram-negative endolysin or ii) a bacteriophage tail/baseplate protein. The present invention relates also to corresponding nucleic acids, vectors, bacteriophages, host cells, and compositions. The present inventions also relates to the use of said polypeptides, nucleic acids, vectors, bacteriophages, host cells, and compositions in methods for treatment of the human or animal body by surgery or therapy or in diagnostic methods practiced on the human or animal body. The polypeptides, nucleic acids, vectors, bacteriophages, host cells, and compositions according to the invention may also be used as an antimicrobial in, e.g., food or feed, in cosmetics, or as disinfecting agent.

II. Description of Related Art

Endolysins are peptidoglycan hydrolases encoded by bacteriophages (i.e. bacterial viruses). They are synthesized during late gene expression in the lytic cycle of phage multiplication and mediate the release of progeny virions from infected cells through degradation of the bacterial peptidoglycan. In terms of enzymatic activity they are usually either ß(1,4)-glycosylases (lysozymes), transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage Cl endolysin towards group A streptococci (Nelson et al., 2001). Since then many publications have established endolysins as an attractive and complementary alternative to control bacterial infections, particularly by Gram positive bacteria. Subsequently different endolysins against other Gram positive pathogens such as Streptococcus pneumoniae (Loeffler et al., 2001), Bacillus anthracis (Schuch et al., 2002), S. agalactiae (Cheng et al., 2005) and Staphylococcus aureus (Rashel et al, 2007) have proven their efficacy as enzybiotics. Nowadays, the most important challenge of endolysin therapy lies in the insensitivity of Gram-negative bacteria towards the exogenous action of endolysins, since the outer membrane shields the access of endolysins from the peptidoglycan.

Gram-negative bacteria possess an outer membrane, with its characteristic asymmetric bilayer as a hallmark. The outer membrane bilayer consists of an inner monolayer containing phospholipids (primarily phosphatidyl ethanolamine) and an outer monolayer that is mainly composed of a single glycolipid, lipopolysaccharide (LPS). There is an immense diversity of LPS structures in the bacterial kingdom and the LPS structure may be modified in response to prevailing environmental conditions. The stability of the LPS layer and interaction between different LPS molecules is mainly achieved by the electrostatic interaction of divalent ions ($Mg^{2+}$, $Ca^{2+}$) with the anionic components of the LPS molecule (phosphate groups in the lipid A and the inner core and carboxyl groups of KDO). Furthermore, the dense and ordered packing of the hydrophobic moiety of lipid A, favored by the absence of unsaturated fatty acids, forms a rigid structure with high viscosity. This makes it less permeable for lipophilic molecules and confers additional stability to the outer membrane (OM).

In contrast to Gram-negative bacteria, Gram-positive bacteria do not possess an outer membrane. The cytoplasmic membrane is surrounded by an up to 25 nm thick layer of peptidoglycan (which is only up to 5 nm for Gram-negative bacteria) which forms the cell wall. Main purpose of the cell wall of Gram-positives is to maintain bacterial shape and to counteract the internal bacterial cell pressure. Peptidoglycan, or murein, is a polymer consisting of sugars and amino acids. The sugar component consists of alternating residues of $\beta$-(1,4) linked N-acetylglucosamine and N-acetylmuramic acid residues compose the sugar components. A peptide chain of three to five amino acids is attached to the N-acetylmuramic acid. The peptide chain can be cross-linked to the peptide chain of another strand forming a 3D mesh-like layer. The peptide chain may contain D- and L-amino acid residues and the composition may vary for different bacteria.

When comparing endolysins originating from phages infecting Gram-positive bacterial species versus those originating from phages infecting Gram-negative bacterial species, a striking difference can be observed, namely the general structure of the endolysins themselves. Phage endolysins of phages infecting Gram-positive bacteria are modular and comprise different individual functional domains or modules. The most common architecture is an N-terminal catalytic domain and a C-terminal cell wall-binding domain (Loessner, 2005). Some Gram-positive endolysins consist of three modules: an N-terminal and central catalytic domain with different specificity and a C-terminal substrate-binding module (Navarre et al., 1999; Pritchard et al., 2004; Yokoi et al., 2005). In contrast, endolysins encoded by phages associated with Gram-negative host cells are typically non-modular but single-module, globular proteins, with only a small number of exceptions. For more information on endolysins as antimicrobials see Nelson et al. ("Endolysins as Antimicrobials", Advances in Virus Research, Volume 83 (2012), p. 299-365, Eds. M. Łobocka and W. Szybalski, Elsevier).

Meanwhile, new strategies have emerged to utilize also endolysins originating from phages infecting Gram-negative bacterial species to control infections caused by Gram-negative bacteria. For this purpose, endolysins of Gram negative bacteria are fused with, e.g. cationic, amphipathic, hydrophobic or antimicrobial peptides. This type of fusion protein allows overcoming previous problems with the outer membrane of Gram-negative bacteria.

However, despite the advances in the art regarding antibacterial agents, there is still a need in the art for further improvement in the design of such antibacterial agents, in particular due to the increasing resistance to conventional antibiotics.

This problem is solved by the subject-matter as set forth below and in the appended claims.

SUMMARY OF THE INVENTION

The inventors of the present invention have surprisingly found that fusing globular Gram-negative endolysins with cell wall binding domains of Gram-negative endolysins or of bacteriophage tail/baseplate proteins yields more effective Gram-negative muralytic enzymes.

Thus, in a first aspect the present invention relates to a polypeptide comprising the amino acid sequence of a Gram-negative globular endolysin and the amino acid sequence of a cell wall binding domain of i) a Gram-negative modular endolysin or ii) a bacteriophage tail/baseplate protein.

Such inventive polypeptide may degrade, usually depending on the components chosen, the cell wall of bacteria selected from the group consisting of *Acinetobacter, Aeromonas, Aggregatibacter, Azospirillum, Bacteroides, Burkholderia, Campylobacter, Candidatus, Caulobacter, Clavibacter, Cronobacter, Delftia, Enterobacter, Erwinia, Escherichia, Flavobacterium, Haemophilus, Iodobacteria, Klebsiella, Kluyvera, Mannheimia, Morganella, Neisseria, Pantoea, Pasteurella, Planktothrix, Pseudoalteromonas, Pseudomonas, Ralstonia, Salmonella, Shigella, Sinorhizobium, Sodalis, Synechococcus, Thalassomonas, Thermus, Vibrio, Xanthomonas, Xylella,* and *Yersinia.*

The inventive polypeptide may additionally comprise at least one amino acid sequence sequence selected from the group consisting of amphiphatic peptides, cationic peptides, hydrophobic peptides, naturally occurring antimicrobial peptides, sushi peptides and defensins. Such further peptide can enhance the antibacterial activity of the inventive polypeptide.

In further aspects, the present invention relates to nucleic acids encoding an inventive polypeptide, vectors or bacteriophages comprising an inventive nucleic acid as well as host cells comprising an inventive polypeptide, nucleic acid, vector, and/or bacteriophage.

The present invention relates in a further aspect also to compositions comprising a polypeptide, nucleic acid, vector, bacteriophage, and/or host cell according to the present invention. Such compositions are preferably pharmaceutical compositions comprising a pharmaceutically acceptable carrier, diluent, or excipient.

Finally, the present invention relates to polypeptides, nucleic acids, vectors, bacteriophages, host cells, compositions and/or kits of the present invention for use in methods of treatment, in particular for the treatment or prevention of bacterial infections.

DESCRIPTION OF ILLUSTRATIVE EMBODIMENTS

I. Definitions

The term "polypeptide" as used herein refers in particular to a polymer of amino acid residues linked by peptide bonds in a specific sequence. The amino acid residues of a polypeptide may be modified by e.g. covalent attachments of various groups such as carbohydrates and phosphate. Other substances may be more loosely associated with the polypeptide, such as heme or lipid, giving rise to conjugated polypeptides which are also comprised by the term "polypeptide" as used herein. The term as used herein is intended to encompass also proteins. Thus, the term "polypeptide" also encompasses for example complexes of two or more amino acid polymer chains. The term "polypeptide" does encompass embodiments of polypeptides which exhibit optionally modifications typically used in the art, e.g. biotinylation, acetylation, pegylation, chemical changes of the amino-, SH- or carboxyl-groups (e.g. protecting groups) etc. As will become apparent from the description below, the polypeptide according to the present invention are fusion proteins, i.e. represent the linkage of at least two amino acid sequences which do not occur in this combination in nature. The term "polypeptide" as used herein is not limited to a specific length of the amino acid polymer chain, but typically the polypeptide will exhibit a length of more than about 150 amino acids. Usually, but not necessarily, a typical polypeptide of the present invention will not exceed about 1000 amino acids in length. The inventive polypeptide may for instance be at most about 750 amino acids long, at most about 500 amino acids long or at most about 300 amino acids long. A possible length range for the inventive polypeptide, without being limited thereto, may thus for example be about 200 to about 750 amino acids, or about 250 to about 600 amino acids. A particularly preferred range is about 250 to about 300 amino acids.

The term "fragment" as used herein refers to an amino acid sequence which is N-terminally, C-terminally, and/or on both termini truncated with respect to the respective reference sequence, for example a given endolysin or SEQ ID NO. Thus, a fragment of an amino acid sequence as used herein is an amino acid sequence which is at least one amino acid shorter than the respective reference sequence. A fragment of an amino acid sequence as used herein is preferably an amino acid sequence which is at most 20, more preferably at most 19, more preferably at most 18, more preferably at most 17, more preferably at most 16, more preferably at most 15, more preferably at most 14, more preferably at most 13, more preferably at most 12, more preferably at most 11, more preferably at most 10, more preferably at most 9, more preferably at most 8, more preferably at most 7, more preferably at most 6, more preferably at most 5, more preferably at most 4, more preferably at most 3, more preferably at most 2, most preferably 1 amino acid residue shorter than the respective reference amino acid sequence. The fragment may for example exhibit vis-à-vis the reference sequence a truncation of 1, 2, 3, 4, 5, 6, 7, 8, 9, 10, 11, 12, 13, 14, 15, 16, 17, 18, 19 or 20 amino acids at the N-terminus, the C-terminus or both. It is understood that a polypeptide comprising a fragment of a given amino acid sequence does not comprise the full length of said reference amino acid sequence.

The term "endolysin" is generally understood be a person skilled in the art. As already mentioned previously, the term refers to a particular type of enzymes encoded in nature by bacteriophages. The bacteriophage utilizes such enzyme to release viral progeny from the inner of the infected bacterial cell. The enzyme hydrolyzes the peptidoglycan in the cell wall, leading to rupture of the bacterial cell. While all endolysins are peptidoglycan degrading enzymes, the actual reaction catalyzed, i.e. the actual bond cleaved in the peptidoglycan of bacteria, may be different. In terms of reaction catalyzed, endolysins may be for example glycosidases, amidases, endopeptidases, or lytic transglycosylases. As will be known by a person skilled in the art, the term "endolysin" does not encompass any enzymes catalyzing the same reactions, but which are not derived from bacteriophages. While such enzymes (e.g., hen egg-white lysozyme) catalyze formally the same reaction, they differ significantly from endolysins, e.g. in terms of biological function, evolutionary background and structure. The term "endolysin", as used herein encompasses naturally occurring endolysins, enzymatically active truncated versions thereof as well as technically modified endolysins deriving from these (i.e. naturally occurring endolysins and their enzymatically active fragments), e.g. with increased heat stability, reduced aggregation etc. Such modified endolysins will usually exhibit a sequence identity of at least 80%, preferably at least 82.5%, more preferably at least 85%, more preferably at least 87.5%, more preferably at least 90%, more preferably at least 92.5%, more preferably at least 95%, more preferably at least 97.5%, or most preferably at least 99% or more with the respective naturally occurring endolysin or its enzymatically active fragment. The term "Gram negative endolysin" refers to endolysins deriving from bacteriophages targeting Gram negative bacteria.

A "modular" endolysin, as used herein, is an endolysin which exhibits at least two distinct functional domains, namely at least one "enzymatically active domain" (EAD) and at least one "cell-wall-binding domain" (CBD). While the former provides the actual enzymatic activity, the latter may provide for target binding. Due to their domain character, these two activities can be separated from each other. Endolysins lacking a distinct CBD do not fall under the term "modular endolysin".

A "cell wall binding domain", or CBD, is an amino acid sequence within an endolysin sequence or phage tail/baseplate protein which folds into a structurally discreet module. The role of a CBD is to bind to the peptidoglycan and direct the catalytic machinery of the full length endolysin or phage tail/baseplate protein onto its substrate, thus enhancing the catalytic efficiency of the multimodular peptidoglycan-degrading enzyme. CBDs are themselves devoid of any catalytic activity.

An "enzymatically active domain" (EAD), as used herein, refers to an amino acid sequence within a modular endolysin sequence which folds into a structurally discreet module. An EAD exerts a catalytic, enzymatic function, i.e. may act for example as endopeptidase, chitinase, T4 like muraminidase, lambda like muraminidase, N-acetyl-muramoyl-L-alanine-amidase (amidase), muramoyl-L-alanine-amidase, muramidase, lytic transglycosylase (C), lytic transglycosylase (M), N-acetyl-muramidase (lysozyme), N-acetyl-glucosaminidase or transglycosylase. Since EADs are derived from modular endolysins, an EAD will exhibit a high degree of sequence identity with a modular endolysin, i.e. will exhibit a sequence identity of at least 95%, more preferably at least 97.5%, or most preferably even 100% with a naturally occurring modular endolysin or its enzymatically active fragment.

As used herein, "globular endolysins" are those endolysins lacking the modular organization and structure of an EAD and a CBD. The term is not intended to encompass fragments of modular endolysins which only retain the enzymatic active domain of a modular endolysin, i.e. an EAD is not a globular endolysin. Hence, a globular endolysin will not exhibit any significant sequence identity with a naturally occurring modular endolysin or its enzymatically active fragment. Usually, a globular endolysin will exhibit less than 90%, more preferably less than 85%, more preferably less than 80%, more preferably less than 75%, more preferably less than 70%, more preferably less than 60%, and most preferably less than 50% or less sequence identity with modular endolysins.

The term "bacteriophage tail/baseplate protein" is generally understood be a person skilled in the art. Tail proteins and baseplate proteins are proteins of bacteriophages. Binding structures located in the tail fiber and/or baseplate of bacteriophages play an important role in mediating injection of the phage genome into the host cell. Tail fiber proteins are positioned at the tip of the tail and are responsible for binding to the cell surface by recognizing a potential host bacterium and attaching to its outer surface. Baseplate proteins control the transfer of the genetic material and can have also cell binding properties. Especially for Myoviruses of Gram negative bacteria (e.g. T4 or P2 phages) different motifs are described which show homology to peptidoglycan binding domains like LysM. Another example is the gp5 of the ICP1 *Vibrio* phage and related proteins encoded in the genome of phages infecting different species like e.g. *Methylobacter* sp. These consist of a peptidoglycan binding domain and an enzymatic active domain, able to degrade the murein layer of the host bacteria.

The term "% sequence identity" is generally understood in the art. Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et a/. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 83, 63-98; Pearson and Lipman (1988), Proc. Natl. Acad. Sci. U. S. A 85, 2444-2448.). Sequences which are identical to other sequences to a certain extent can be identified by these programs. Furthermore, programs available in the Wisconsin Sequence Analysis Package, version 9.1 (Devereux et al, 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences. If herein reference is made to an amino acid sequence sharing a particular extent of sequence identity to a reference sequence, then said difference in sequence is preferably due to conservative amino acid substitutions. Preferably, such sequence retains the activity of the reference sequence, e.g. retains the activity of degrading the peptidoglycan layer of Gram-negative bacteria, albeit maybe at a slower rate. In addition, if reference is made herein to a sequence sharing "at least" at certain percentage of sequence identity, then 100% sequence identity are preferably not encompassed.

As used herein, the term "cationic peptide" refers preferably to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides, but also includes cationic peptides which comprise for example less than 20%, preferably less than 10% positively charged amino acid residues.

The term "polycationic peptide", as used herein, refers preferably to a peptide composed of mostly positively charged amino acid residues, in particular lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term, "antimicrobial peptide" (AMP), as used herein, refers preferably to any naturally occurring peptide that has microbicidal and/or microbistatic activity on for example bacteria, viruses, fungi, yeasts, *mycoplasma* and protozoa. Thus, the term "antimicrobial peptide" as used herein refers in particular to any peptide having anti-bacterial, antifungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties. Preferred are anti-bacterial peptides. The antimicrobial peptide may be a member of the RNase A super family, a defensin, cathelicidin, granulysin, histatin, psoriasin, dermicidine or hepcidin. The antimicrobial peptide may be naturally occurring in insects, fish, plants, arachnids, vertebrates or mammals. Preferably the antimicrobial peptide may be naturally occurring in insects, fish, plants, arachnids, vertebrates or mammals. Preferably the antimicrobial peptide may be naturally occurring in radish, silk moth, wolf spider, frog, preferably in *Xenopus laevis*, *Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human. As used herein, an "antimicrobial peptide" (AMP) may in particular be a peptide which is not a cationic peptide, polycationic peptide, amphipathic peptide, sushi peptide, defensins, and hydrophobic peptide, but nevertheless exhibits antimicrobial activity.

The term "sushi peptide", as used herein, refers to complement control proteins (CCP) having short consensus repeats. The sushi module of sushi peptides functions as a protein-protein interaction domain in many different proteins. Peptides containing a Sushi domain have been shown to have antimicrobial activities. Preferably, sushi peptides are naturally occurring peptides.

The term "amphipathic peptide", as used herein, refers to synthetic peptides having both hydrophilic and hydrophobic functional groups. Preferably, the term "amphipathic peptide" as used herein refers to a peptide having a defined arrangement of hydrophilic and hydrophobic groups e.g. amphipathic peptides may be e.g. alpha helical, having predominantly non polar side chains along one side of the helix and polar residues along the rest of its surface.

The term "hydrophobic group", as used herein, refers preferably to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a non-aqueous environment. Examples of amino acid residues with hydrophobic side chains are valine, isoleucine, leucine, methionine, phenylalanine, tryptophan, cysteine, alanine, tyrosine, and proline residues.

The term "hydrophobic peptide", as used herein, refers to a hydrophobic peptide, which is preferably composed of mostly amino acid residues with hydrophobic groups. Such peptide is preferably composed of mostly hydrophobic amino acid residues, i.e. at least about 20, 30, 40, 50, 60, 70, 75, 80, 85, 90, 95 or at least about 100% of the amino acid residues are hydrophobic amino acid residues. The amino acid residues being not hydrophobic are preferably neutral and preferably not hydrophilic.

The term "comprising", as used herein, shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The use of the word "a" or "an", when used herein, may mean "one," but it is also consistent with the meaning of "one or more," "at least one," and "one or more than one."

II. Polypeptides

As already mentioned, the present invention relates in a first aspect to a polypeptide comprising the amino acid sequence of a Gram-negative globular endolysin and the amino acid sequence of a cell wall binding domain of i) a Gram-negative modular endolysin or ii) a bacteriophage tail/baseplate protein.

Endolysins are well known to a person skilled in the art of antimicrobial agents. Many of these proteins have been sequenced and their structure and domain architecture (including CBDs and EADs) analyzed. Usually it is thus very simple to elucidate the presence of a cell wall binding domain in a given endolysin sequence, for example on basis of homology analyses. In case of doubt, whether a given sequence of an endolysin acts as cell wall binding domain or not, said property can also be analyzed by routine test known in the art. Exemplary tests are provided for instance in Mol Microbiol. 2002 April; 44(2):335-49 and Briers et al. (Mol Microbiol. 2007 September; 65(5):1334-44). Briefly, the candidate cell wall-binding domain is fused (e.g. N-terminally) to green fluorescent protein (GFP). Subsequently, the GFP-fusion protein is incubated with the target bacteria of the parent endolysin. If these are gram-negative bacteria, then the outer membrane is permeabilized in advance by treatment with a chloroform-saturated buffer (chloroform-saturated 0.05 M Tris-buffer (pH 7.7), 45 min (Lavigne et al., Cell Mol Life Sci. 2004 November; 61(21):2753-9). The candidate CBD-GFP fusion is then added to the permeabilized cells (e.g. final concentration 5 µM). Purified recombinant GFP is used in the negative control. This mixture is then incubated, e.g. for 5 min at 25° C., subsequently spun down and the supernatant discarded. The cell pellet may then be washed (e.g. twice in the corresponding buffer) and analyzed for GFP-binding via suitable means such as epifluorescence microscopy, flow cytometry or confocal fluorescence microscopy. In addition, a specific peptidoglycan binding test can be performed Briers et al. (Mol Microbiol. 2007 September; 65(5):1334-44). For this purpose murein of the target bacteria is isolated and contacted with the candidate CBD-GFP fusion protein and binding is once again analyzed, e.g. via epifluorescence microscopy.

Exemplary cell wall binding domains of Gram-negative endolysins, which may be used in carrying out the present invention, are cell wall binding domains deriving from the endolysins of bacteriophages ΦKZ and EL, or from the endolysins OBPgpLYS, PVPSE1gp146, and 201φ2-1.

Phage baseplate/tail proteins are also known in the art and information on sequence, structure and domain architecture is frequently available. Otherwise, similar tests as mentioned above for endolysins are suited to identify cell wall binding domains of bacteriophage tail/baseplate proteins. An exemplary cell wall binding domain of bacteriophage tail/baseplate protein, which may be used in carrying out the present invention, is the cell wall binding domains deriving from the baseplate protein of *Vibrio* phage ICP1 (see YP_004251150.1) or *Vibrio* phage RYC (BAV80844.1).

Examples for specific sequences comprising cell wall binding domains (deriving from Gram-negative endolysins or bacteriophage tail/baseplate proteins) are provided herein in SEQ ID Nos: 1, 2, 3, 4, 5, 6, 7, 8, 9, 10, 11, 12, 13, 14, 15, 16, and 17, and sequences having at least 80% sequence identity to any of these while retaining the property of cell wall binding. Particularly preferred sequences are SEQ ID Nos: 1, 2, 3, 4, 5, 6, 7, 8, 9, 10, 11, 12, 13 and 14, and sequences having at least 80% sequence identity to any of these while retaining the property of cell wall binding. Most preferred are sequences deriving from the cell wall binding domain of KZ144 endolysin, such as SEQ ID Nos: 1, 2, 3, 4, 5, 6, 7, and 8, and sequences having at least 80% sequence identity to any of these while retaining the property of cell wall binding.

As previously mentioned, the inventive polypeptide comprises aside of the amino acid sequence of a cell wall binding domain of a Gram-negative modular endolysin or a bacteriophage baseplate tail protein also the amino acid sequence of a Gram-negative globular endolysin. A person skilled in the art will be readily able to ascertain whether a given polypeptide derives from a Gram-negative endolysin exhibiting a cell wall binding domain (i.e. is a modular endolysin) or derives from a Gram-negative endolysin which does not exhibit such domain structure (globular endolysin). Examples for globular endolysins are for example provided in Table 1 below.

TABLE 1

Examples for globular endolysins

| Host | Phage name | Protein ID |
|---|---|---|
| *Acinetobacter* | *Acinetobacter* phage Ac42 | YP_004009379.1 |
| *Acinetobacter* | *Acinetobacter* phage Acj61 | YP_004009630.1 |
| *Acinetobacter* | *Acinetobacter* phage Acj9 | YP_004010153.1 |
| Aeromonas | Aeromonas phage PX29 | ADQ53036.1 |
| Aeromonas | Aeromonas phage PAS-1 | AEM36042.1 |
| Aeromonas | Aeromonas phage phiAS7 | AEZ65050.1 |
| Aeromonas | Aeromonas phage phiAS4 | YP_003969005.1 |
| Aeromonas | Aeromonas phage 44RR2.8t | NP_932578.1 |
| Aeromonas | Aeromonas phage 25 | YP_656449.1 |
| Aeromonas | Aeromonas phage 31 | YP_238949.1 |
| Aeromonas | Aeromonas phage Aeh1 | NP_944217.1 |
| Aeromonas | Aeromonas phage phiO18P | YP_001285657.1 |
| Aeromonas | Aeromonas phage 65 | YP_004300997.1 |
| Aeromonas | Aeromonas phage phiAS5 | YP_003969406.1 |
| Azospirillum | Azospirillum phage Cd | YP_001686894.1 |
| Aggregatibacter | Aggregatibacter phage S1249 | YP_003344813.1 |
| Bacteroides | Bacteroides phage B40-8 | YP_002221548.1 |
| Bacteroides | Bacteroides phage B124-14 | YP_005102482.1 |
| Burkholderia | Burkholderia phage BcepF1 | YP_001039778.1 |
| Burkholderia | Burkholderia phage BcepB1A | YP_024909.1 |
| Burkholderia | Burkholderia phage Bcep22 | YP_001531197.1 |
| Burkholderia | Burkholderia phage BcepNazgul | NP_918971.2 |
| Burkholderia | Burkholderia phage phiE255 | YP_001111252.1 |
| Burkholderia | Burkholderia phage KS9 | YP_003090199.1 |
| Burkholderia | Burkholderia phage phi1026b | NP_945054.1 |
| Burkholderia | Burkholderia phage phiE125 | NP_536381.1 |
| Burkholderia | Burkholderia phage BcepC6B | YP_024942.1 |
| Burkholderia | Burkholderia phage Bcep176 | YP_355393.1 |
| Burkholderia | Burkholderia phage BcepIL02 | YP_002922746.1 |
| Burkholderia | Burkholderia phage BcepMu | YP_024695.1 |
| Burkholderia | Burkholderia phage KS10 | YP_002221425.1 |
| Burkholderia | Burkholderia phage phi644-2 | YP_001111104.1 |

TABLE 1-continued

Examples for globular endolysins

| Host | Phage name | Protein ID |
|---|---|---|
| Campylobacter | Campylobacter phage CP220 | CBJ93929.1 |
| Campylobacter | Campylobacter phage CPt10 | CBJ94327.1 |
| Candidatus | Acyrthosiphon pisum bacteriophage APSE-1 | NP_050974.1 |
| Candidatus | Bacteriophage APSE-2 | ACJ10174.1 |
| Candidatus | Bacteriophage APSE-4 | ACJ10096.1 |
| Candidatus | Bacteriophage APSE-7 | ACJ10111.1 |
| Candidatus | Bacteriophage APSE-5 | ACJ10082.1 |
| Candidatus | Bacteriophage APSE-3 | ACJ10123.1 |
| Candidatus | Bacteriophage APSE-6 | ACJ10136.1 |
| Caulobacter | Caulobacter phage Cd1 | ADD21680.1 |
| Cronobacter | Cronobacter phage ENT47670 | ADZ13641.1 |
| Cronobacter | Cronobacter phage ESP2949-1 | AEM24793.1 |
| Cronobacter | Cronobacter phage ES2 | AEM24706.1 |
| Cronobacter | Cronobacter phage ENT39118 | ADZ13601.1 |
| Delftia | Deftia phage phiW-14 | YP_003358866.1 |
| Enterobacter | Enterobacteria phage F20 | AEQ39188.1 |
| Escherichia | Escherichia phage TL-2011b | AEW24559.1 |
| Escherichia | Escherichia phage vB_EcoM_ECO1230-10 | ADE87938.1 |
| Escherichia | Escherichia phage HK639 | YP_004934099.1 |
| Escherichia | Escherichia phage phiV10 | YP_512283.1 |
| Escherichia | Escherichia phage rv5 | YP_002003587.1 |
| Escherichia | Escherichia phage K1H | ADA82342.1 |
| Escherichia | Escherichia phage K1ind3 | ADA82488.1 |
| Escherichia | Escherichia phage K1G | ADA82292.1 |
| Escherichia | Escherichia phage wV7 | AEM00790.1 |
| Escherichia | Escherichia phage HK75 | YP_004934160.1 |
| Escherichia | Stx2-converting phage 1717 | YP_002274257.1 |
| Escherichia | Stx2-converting phage 86 | YP_794054.1 |
| Escherichia | Stx2 converting phage II | YP_003828995.1 |
| Escherichia | Escherichia phage phiEB49 | AEI91208.1 |
| Escherichia | Enterobacteria phage T1 | YP_003933.1 |
| Escherichia | Enterobacteria phage T3 | NP_523313.1 |
| Escherichia | Enterobacteria phage T4 | NP_049736.1 |
| Escherichia | Enterobacteria phage T5 | YP_006868.1 |
| Escherichia | Enterobacteria phage TLS | YP_001285558.1 |
| Escherichia | Enterobacteria phage vB_EcoM-VR7 | YP_004063811.1 |
| Escherichia | Enterobacteria phage WV8 | YP_002922821.1 |
| Escherichia | Enterobacteria phage Min27 | ABY49900.1 |
| Escherichia | Enterobacteria phage lambda | NP_040645.1 |
| Escherichia | Enterobacteria phage K1F | YP_338105.1 |
| Escherichia | Enterobacteria phage IME10 | AER08021.1 |
| Escherichia | Enterobacteria phage vB_EcoM-FV3 | AEZ65218.1 |
| Escherichia | Escherichia phage TL-2011c | AEW24625.1 |
| Escherichia | Enterobacteria phage Bp7 | AEN93735.1 |
| Escherichia | Enterobacteria phage RB49 | NP_891673.1 |
| Escherichia | Enterobacteria phage RTP | YP_399008.1 |
| Escherichia | Enterobacteria phage BP-4795 | YP_001449285.1 |
| Escherichia | Enterobacteria phage BA14 | YP_002003466.1 |
| Escherichia | Enterobacteria phage 285P | YP_004300550.1 |
| Escherichia | Enterobacteria phage P1 | YP_006484.1 |
| Escherichia | Enterobacteria phage JS98 | YP_001595245.1 |
| Escherichia | Enterobacteria phage AR1 | BAI83135.1 |
| Escherichia | Enterobacteria phage SfV | NP_599082.1 |
| Escherichia | Enterobacteria phage T7 | NP_041973.1 |
| Escherichia | Enterobacteria phage phiEco32 | YP_001671762.1 |
| Escherichia | Enterobacteria phage A5 | ABF71471.1 |
| Escherichia | Enterobacteria phage 186 | AAC34155.1 |
| Escherichia | Enterobacteria phage HK022 | AAF30387.1 |
| Escherichia | Enterobacteria phage JS10 | YP_002922463.1 |
| Escherichia | Enterobacteria phage P2 | NP_046765.1 |
| Escherichia | Enterobacteria phage 933W (sensu lato) | NP_049505.1 |
| Escherichia | Enterobacteria phage JK06 | YP_277498.1 |
| Escherichia | Enterobacteria phage N15 | NP_046950.1 |
| Escherichia | Enterobacteria phage K1E | YP_425023.1 |
| Escherichia | Enterobacteria phage K1-5 | YP_654144.1 |
| Escherichia | Enterobacteria phage JSE | YP_002922178.1 |
| Escherichia | Enterobacteria phage IME08 | YP_003734260.1 |
| Escherichia | Enterobacteria phage HK97 | NP_037753.1 |
| Escherichia | Enterobacteria phage RB43 | YP_239135.1 |
| Escherichia | Enterobacteria phage RB16 | YP_003858447.1 |
| Escherichia | Enterobacteria phage phi27 | NP_543082.1 |
| Escherichia | Enterobacteria phage phiEcoM-GJ1 | YP_001595416.1 |
| Escherichia | Enterobacteria phage Phi1 | YP_001469446.1 |
| Escherichia | Enterobacteria phage EcoDS1 | YP_002003756.1 |
| Escherichia | Enterobacteria phage cdtI | YP_001272571.1 |
| Escherichia | Enterobacteria phage CC31 | YP_004009990.1 |

TABLE 1-continued

Examples for globular endolysins

| Host | Phage name | Protein ID |
|---|---|---|
| *Escherichia* | Enterobacteria phage K30 | YP_004678738.1 |
| *Escherichia* | Enterobacteria phage CUS-3 | ABQ88407.1 |
| *Escherichia* | Stx1 converting phage | BAC77971.1 |
| *Escherichia* | Stx2 converting phage I | BAB88004.1 |
| *Escherichia* | Stx1-converting phage phi-O153 | AAW21764.1 |
| *Escherichia* | *Escherichia* phage D108 | YP_003335769.1 |
| *Escherichia* | Enterobacteria phage SPC35 | YP_004306522.1 |
| *Escherichia* | Enterobacteria phage Mu | NP_050626.1 |
| *Escherichia* | Enterobacteria phage RB69 | NP_861818.1 |
| *Escherichia* | Enterobacteria phage RB14 | YP_002854463.1 |
| *Escherichia* | Enterobacteria phage RB32 | ABI94948.1 |
| *Escherichia* | Enterobacteria phage RB51 | YP_002854084.1 |
| Erwinia | Erwinia phage phiEa116 | CCA66256.1 |
| Erwinia | Erwinia phage vB_EamM-M7 | AEJ81266.1 |
| Erwinia | Erwinia phage vB_EamM-Y2 | AEJ81402.1 |
| Erwinia | Erwinia phage vB_EamP-L1 | AEJ81484.1 |
| Erwinia | Erwinia phage phiEa21-4 | YP_002456060.1 |
| Erwinia | Erwinia phage phiEa104 | YP_004327012.1 |
| Erwinia | Erwinia phage Era103 | YP_001039680.1 |
| Flavobacterium | Flavobacterium phage 11b | YP_112524.1 |
| Haemophilus | Haemophilus phage SuMu | AEG42272.1 |
| Haemophilus | Haemophilus phage HP1 | NP_043495.1 |
| Haemophilus | Haemophilus phage HP2 | NP_536831.1 |
| Haemophilus | Haemophilus phage Aaphi23 | NP_852750.1 |
| Iodobacteria | Iodobacteriophage phiPLPE | YP_002128449.1 |
| *Klebsiella* | *Klebsiella* phage K11 | YP_002003804.1 |
| *Klebsiella* | *Klebsiella* phage KP32 | YP_003347533.1 |
| *Klebsiella* | *Klebsiella* phage KP15 | YP_003580002.1 |
| *Klebsiella* | Enterobacteria phage vB_KleM-RaK2 | AFA44346.1 |
| Kluyvera | Kluyvera phage Kvp1 | YP_002308397.1 |
| Mannheimia | Mannheimia phage phiMHaA1 | YP_655477.1 |
| Mannheimia | Mannheimia phage phiMhaA1-PHL101 | ABD90561.1 |
| Morganella | Morganella phage MmP1 | YP_002048642.1 |
| Alphaproteobacteria | Phage phiJL001 | YP_224014.1 |
| Pseudoalteromonas | Pseudoalteromonas phage H105/1 | YP_004327143.1 |
| *Pseudomonas* | *Pseudomonas* phage LKA1 | YP_001522894.1 |
| *Pseudomonas* | *Pseudomonas* phage D3 | NP_061527.1 |
| *Pseudomonas* | *Pseudomonas* phage F10 | YP_001293405.1 |
| *Pseudomonas* | *Pseudomonas* phage F116 | YP_164326.1 |
| *Pseudomonas* | *Pseudomonas* phage F8 | YP_001294463.1 |
| *Pseudomonas* | *Pseudomonas* phage gh-1 | NP_813758.1 |
| *Pseudomonas* | *Pseudomonas* phage LBL3 | YP_002154189.1 |
| *Pseudomonas* | *Pseudomonas* phage LKD16 | YP_001522837.1 |
| *Pseudomonas* | *Pseudomonas* phage LMA2 | YP_002154280.1 |
| *Pseudomonas* | *Pseudomonas* phage LUZ19 | YP_001671990.1 |
| *Pseudomonas* | *Pseudomonas* phage PA11 | YP_001294626.1 |
| *Pseudomonas* | *Pseudomonas* phage PAJU2 | YP_002284361.1 |
| *Pseudomonas* | *Pseudomonas* phage PaP3 | NP_775256.1 |
| *Pseudomonas* | *Pseudomonas* phage PB1 | YP_002455978.1 |
| *Pseudomonas* | *Pseudomonas* phage phi13 (S-segment) | NP_690810.1 |
| *Pseudomonas* | *Pseudomonas* phage phi15 | YP_004286199.1 |
| *Pseudomonas* | *Pseudomonas* phage phi-2 | YP_003345505.1 |
| *Pseudomonas* | *Pseudomonas* phage phiIBB-PF7A | YP_004306332.1 |
| *Pseudomonas* | *Pseudomonas* phage phikF77 | YP_002727868.1 |
| *Pseudomonas* | *Pseudomonas* phage PT2 | YP_002117830.1 |
| *Pseudomonas* | *Pseudomonas* phage PT5 | YP_002117771.1 |
| *Pseudomonas* | *Pseudomonas* phage SN | YP_002418854.1 |
| *Pseudomonas* | *Pseudomonas* phage phi297 | YP_005098091.1 |
| *Pseudomonas* | *Pseudomonas* phage Bf7 | YP_005098158.1 |
| *Pseudomonas* | *Pseudomonas* phage PaP1 | AEK21612.1 |
| *Pseudomonas* | *Pseudomonas*LUZ24 | YP_001671940.1 |
| *Pseudomonas* | *Pseudomonas* phage phi-6 segment S | NP_620343.1 |
| *Pseudomonas* | *Pseudomonas* phage vB_PaeS_PMG1 | YP_005098234.1 |
| *Pseudomonas* | Enterobacteria phage phiKMV | NP_877484.1 |
| Pasteurella | Pasteurella phage F108 | YP_654740.1 |
| Ralstonia | Ralstonia phage RSB2 | BAJ51815.1 |
| *Salmonella* | *Salmonella* phage SETP3 | YP_001110823.1 |
| *Salmonella* | Bacteriophage PS3 | CAA09701.1 |
| *Salmonella* | Enterobacteria phage ST104 | YP_006397.1 |
| *Salmonella* | Enterobacteria phage SP6 | AAR90036.1 |
| *Salmonella* | Enterobacteria phage Felix 01 | NP_944846.1 |
| *Salmonella* | Enterobacteria phage P22 | DAA01040.1 |
| *Salmonella* | Bacteriophage Wphi | AAN28227.1 |
| *Salmonella* | Enterobacteria phage EPS7 | YP_001836966.1 |
| *Salmonella* | Enterobacteria phage Fels-2 | YP_001718740.1 |
| *Salmonella* | *Salmonella* phage ES18 | YP_224214.1 |

TABLE 1-continued

Examples for globular endolysins

| Host | Phage name | Protein ID |
|---|---|---|
| *Salmonella* | *Salmonella* phage PsP3 | NP_958065.1 |
| *Salmonella* | *Salmonella* phage E1 | YP_001742044.1 |
| *Salmonella* | *Salmonella* phage SETP12 | ABN70688.1 |
| *Salmonella* | *Salmonella* phage SETP5 | ABN70687.1 |
| *Salmonella* | *Salmonella* phage HK620 | NP_112069.1 |
| *Salmonella* | *Salmonella* phage RE-2010 | ADQ92398.1 |
| *Salmonella* | Phage Gifsy-1 | YP_001700616.1 |
| *Salmonella* | Phage Gifsy-2 | YP_001700672.1 |
| *Salmonella* | *Salmonella* phage c341 | YP_003090277.1 |
| *Salmonella* | *Salmonella* phage epsilon15 | NP_848233.1 |
| *Salmonella* | *Salmonella* phage epsilon34 | YP_002533525.1 |
| *Salmonella* | *Salmonella* phage Fels-1 | YP_001700560.1 |
| *Salmonella* | *Salmonella* phage phiSG-JL2 | YP_001949762.1 |
| *Salmonella* | *Salmonella* phage SE1 | YP_002455881.1 |
| *Salmonella* | *Salmonella* phage ST64B | NP_700425.1 |
| *Salmonella* | *Salmonella* phage ST64T | NP_720320.1 |
| *Salmonella* | *Salmonella* phage Vi06 | YP_004306666.1 |
| *Salmonella* | *Salmonella* phage SPN1S | YP_005098003.1 |
| *Salmonella* | *Salmonella* phage SE2 | YP_005098118.1 |
| *Salmonella* | *Salmonella* phage SS3e | YP_005097816.1 |
| *Salmonella* | *Salmonella* Phage PS34 | O80288.1 |
| *Salmonella* | Enterobacteria phage 13a | YP_002003950.1 |
| Shigella | Shigella phage Sf6 | NP_958236.1 |
| Shigella | Shigella phage Shfl1 | YP_004414884.1 |
| Shigella | Shigella phage Shfl2 | YP_004415022.1 |
| Shigella | Shigella phage EP23 | YP_004957490.1 |
| Sinorhizobium | Sinorhizobium phage PBC5 | NP_542265.1 |
| Sodalis | Sodalis phage phiSG1 | YP_516184.1 |
| Sodalis | Sodalis phage SO-1 | YP_003344991.1 |
| Synechococcus | Synechococcus phage S-CBS2 | YP_004421540.1 |
| Synechococcus | Synechococcus phage S-CRM01 | YP_004508546.1 |
| Synechococcus | Synechococcus phage S-PM2 | YP_195189.2 |
| Synechococcus | Synechococcus phage S-PM2 (another) | YP_195188.1 |
| Thalassomonas | Thalassomonas phage BA3 | YP_001552293.1 |
| Thermus | Thermus phage P23-45 | YP_001467961.1 |
| Thermus | Thermus phage P23-77 | YP_003169716.1 |
| Thermus | Thermus phage P23-77 (another) | YP_003169717.1 |
| Thermus | Thermus phage P74-26 | YP_001468077.1 |
| Vibrio | Vibrio phage ICP3 | YP_004251275.1 |
| Vibrio | Vibrio phage K139 | NP_536660.1 |
| Vibrio | Vibrio phage kappa | YP_001650899.1 |
| Vibrio | Vibrio phage N4 | YP_003347926.1 |
| Vibrio | Vibrio phage VP93 | YP_002875665.1 |
| Vibrio | Vibrio phage ICP3_2009_B | ADX87518.1 |
| Vibrio | Vibriophage VP4 | YP_249586.1 |
| Vibrio | Vibrio phage ICP3_2007_A | ADX87661.1 |
| Xanthomonas | Xanthomonas phage OP1 | YP_453585.1 |
| Xanthomonas | Xanthomonas phage phiL7 | YP_002922642.1 |
| Xanthomonas | Xanthomonas phage Xop411 | YP_001285697.1 |
| Xanthomonas | Xanthomonas phage Xp10 | NP_858975.1 |
| Xylella | Xylella phage Xfas53 | YP_003344916.1 |
| Yersinia | Yersinia pestis phage phiA1122 | NP_848277.1 |
| Yersinia | Yersinia phage Berlin | YP_918995.1 |
| Yersinia | Yersinia phage L-413C | NP_839858.1 |
| Yersinia | Yersinia phage phiR1-37 | YP_004934318.1 |
| Yersinia | Yersinia phage phiYeO3-12 | NP_052084.1 |
| Yersinia | Yersinia phage PY54 | NP_892107.1 |
| Yersinia | Yersinia phage Yepe2 | YP_002003326.1 |
| Yersinia | Yersinia phage PY100 | CAJ28446.1 |
| Yersinia | Yersinia phage Yep-phi | ADQ83168.1 |
| *Acinetobacter* | *Acinetobacter* phage vB_AbaP_CEB1 | ALC76575.1 |
| *Salmonella* | *Salmonella* phage phi68 | AHY18890.1 |
| *Salmonella* | *Salmonella* phage SPN9CC | YP_006383882 |
| *Acinetobacter* | *Acinetobacter* phage vB_AbaP_Acibel007 | YP_009103259.1 |
| *Acinetobacter* | *Acinetobacter* phage Abp1 | AFV51025.1 |
| *Pseudomonas* | *Pseudomonas aeruginosa* phage LUZ7 | YP_003358335.1 |
| *Pseudomonas* | *Pseudomonas aeruginosa* phage LIT1 | YP_003358446.1 |
| *Pseudomonas* | *Pseudomonas* phage vB_PaeP_C2-10_Ab09 | YP_009031822.1 |
| *Pseudomonas* | *Pseudomonas* phage 2b.1b | SEQ ID NO: 18 |
| *Salmonella* | *Salmonella* phage SBA-1781 | AFU63467.1 |
| *Salmonella* | *Salmonella* phage Shivani | AJA73488.1 |

The sequences of the globular endolysins of table 1 may be accessed for instance via the protein database of NCBI. It is understood that the sequences of the endolysins listed in table 1 may also be modified, e.g. may lack the N-terminal methionine to avoid a further start codon in the corresponding nucleic acid sequence. Using such marginally amended sequences is also within the scope of the present invention and it is understood, that when reference herein is made to endolysins of table 1, that also such modified endolysins are encompassed by said definition.

Particularly preferred sequences of globular endolysins, which may be used in carrying out the present invention, are sequences deriving from globular endolysins Abgp46, Lys68 of *Salmonella* phage phi68 and Lys394 endolysin. Exemplary sequences are provided as SEQ ID Nos. 18, 19, 20, 21, 22, 23, 24, 25, 26, 27 and 28.

The sequence of the cell wall binding domain (e.g. of the Gram-negative modular endolysin) and the sequence of the Gram-negative globular endolysin may be linked directly to each other or via an intermediate linker sequence, the linker sequence preferably not exceeding more than 50 amino acids in length, more preferably not more than 30 amino acids in length, even more preferably not more than 20 amino acids in length. Preferably, the cell wall binding domain is situated N-terminal of the sequence of the globular endolysin, i.e. of the domain with the enzymatic activity.

Non-limiting examples of polypeptides according to the present invention are provided in SEQ ID Nos. 29, 30, 31, 32, 33 and 34. If such sequence is to be combined with a further amino acid sequence stretch as defined further below, and said further amino acid sequence stretch is positioned N-terminal of the unit formed by the cell wall binding domain and globular endolysin sequences, said sequences are preferably used without methionine start codon (see SEQ ID Nos. 35, 36, 37, 38, 39 and 40)

A polypeptide according to the present invention exhibits preferably the activity of a peptidoglycan degrading enzyme, i.e. is capable of degrading bacterial peptidoglycan. Typically a polypeptide of the present invention will be capable of degrading the peptidoglycan of at least one type of Gram-negative bacteria, such as *K. pneumoniae, E. coli* or *P. aeruginosa*. The peptidoglycan degrading activity on gram negative bacteria can be measured by assays well known in the art, e.g. by muralytic assays in which the outer membrane of gram negative bacteria is permeabilized or removed (e.g. with chloroform) to allow the putative enzyme access to the peptidoglycan layer. If the enzyme is active, degradation of the peptidoglycan layer will lead to a drop of turbidity, which can be measured photometrically (see for example Briers et al., *J. Biochem. Biophys Methods* 70: 531-533, (2007).

A polypeptide according to the present invention may comprise additionally at least one further amino acid sequence stretch selected from the group consisting of amphipathic peptide, cationic peptide, polycationic peptide, hydrophobic peptide, or naturally occurring antimicrobial peptide, like sushi peptide and defensin. This additional at least one amino acid sequence stretch may in principle be present at any position in the inventive polypeptide, but is preferably present at the termini, i.e. in the N- or C-terminal region of the inventive polypeptide. Thus, this additional amino acid sequence stretch is preferably not positioned between the sequence of the cell wall binding domain (e.g. of the Gram-negative modular endolysin) and the sequence of the Gram-negative globular endolysin. Such additional amino acid sequence stretch may be fused directly, or via a peptide linker, to the rest of the polypeptide. It is understood that if one (or more) such additional amino acid sequence stretches according to the present invention are present in the N-terminal region of the inventive polypeptide, then there may be further additional amino acids on the N-terminus of the additional amino acid sequence stretch. Preferably these comprise the amino acid methionine (Met), or the sequence methionine, glycine and serine (Met-Gly-Ser).

This at least one additional amino acid sequence stretch preferably has the function to lead the inventive polypeptide through the outer membrane of bacteria and may have activity or may have no or only low activity when administered without being fused to the polypeptide of the invention. The function to guide the polypeptide through the outer membrane of Gram-negative bacteria is caused by the outer membrane or LPS disrupting, permeabilising or destabilizing activity of said amino acid sequence stretches.

Such outer membrane or LPS disrupting or permeabilising or destabilizing activity of these amino acid sequence stretches may be preferably determined in a method as follows: Exponentially growing Gram-negative cells are incubated at room temperature with protein (candidate polypeptide of the present invention exhibiting at least one additional amino acid sequence stretch) at a final concentration of 100 µg/ml in buffer (20 mM $NaH_2PO_4$—NaOH pH7.4; 0.5 M NaCl; 0.5 M imidazole) and a cell density of ~$10^6$/ml. After 1 hour the cell suspension is diluted in PBS buffer ($10^{-5}$, $10^{-4}$ and $10^{-3}$), plated (standard LB-medium) and incubated overnight at 37° C. Additionally, negative controls containing cells in PBS buffer or cells incubated with the matching polypeptide without the additional amino acid sequence stretch) are plated. The residual colonies are counted after the overnight incubation for each plate. If the protein exhibits such outer membrane or LPS disrupting or permeabilising or destabilizing activity, the bacteria cells are lysed due to the treatment with the polypeptide and thus, the number of the bacteria colonies on the agar plate is reduced. Thus, the reduction in the number of bacteria colonies after treatment with the protein is indicative for an outer membrane or LPS disrupting or permeabilising or destabilizing activity of the polypeptide.

Especially preferred are cationic and/or polycationic amino acid sequence stretches comprising at least one motive according to SEQ ID NO:41 (KRKKRK). In particular cationic amino acid sequence stretches comprising at least 2, 3, 4, 5, 6, 7, 8, 9, 10, 11, 12, 13, 14, 15, 16 or 17 motives according to SEQ ID NO: 41 (KRKKRK) are preferred. More preferred are cationic peptide stretches comprising at least one KRK motive (lys-arg-lys), preferable at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 KRK motives.

In another preferred embodiment of the present invention the cationic amino acid sequence stretch comprises beside the positively charged amino acid residues, in particular lysine and/or arginine residues, neutrally charged amino acid residues, in particular glycine and/or serine residues. Preferred are cationic amino acid sequence stretches consisting of about 70% to about 100%, or about 80% to about 95%, or about 85% to about 90% positively charged amino acid residues, in particular lysine, arginine and/or histidine residues, more preferably lysine and/or arginine residues and of about 0% to about 30%, or about 5% to about 20%, or about 10% to about 20% neutrally charged amino acid residues, in particular glycine and/or serine residues. Preferred are amino acid sequence stretches consisting of about 4% to about 8% serine residues, of about 33% to about 36% arginine residues and of about 56% to about 63% lysine residues. Especially preferred are amino acid sequence stretches comprising at least one motive according to SEQ ID NO: 42 (KRXKR), wherein X is any other amino acid than lysine, arginine and histidine. Especially preferred are polypeptide stretches comprising at least one motive according to SEQ ID NO: 43 (KRSKR). More preferred are cationic stretches comprising at least about 2, 3, 4, 5, 6, 7, 8, 9, 10, 11, 12, 13, 14, 15, 16, 17, 18, 19 or at least about 20 motives according to SEQ ID NO: 42 (KRXKR) or SEQ ID NO: 43 (KRSKR).

Also preferred are amino acid sequence stretches consisting of about 9 to about 16% glycine residues, of about 4 to about 11 serine residues, of about 26 to about 32% arginine residues and of about 47 to about 55% lysine residues. Especially preferred are amino acid sequence stretches comprising at least one motive according to SEQ ID NO: 44 (KRGSG). More preferred are cationic stretches comprising at least about 2, 3, 4, 5, 6, 7, 8, 9, 10, 11, 12, 13, 14, 15, 16, 17, 18, 19 or at least bout 20 motives according to SEQ ID NO: 44 (KRGSG).

In another preferred embodiment of the present invention such cationic amino acid sequence stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Preferred are cationic amino acid sequence stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Examples for cationic and polycationic amino acid sequence stretches are listed in the following table:

TABLE 2

| amino acid sequence stretch | length | SEQ ID NO: |
|---|---|---|
| KRKKRK | 6 | 41 |
| KRKKRKKRK | 9 | 45 |
| RRRRRRRRR | 9 | 46 |
| KKKKKKKK | 8 | 47 |
| KRKKRKKRKK | 10 | 48 |
| KRKKRKKRKKRK | 12 | 49 |
| KRKKRKKRKKRKKR | 14 | 50 |
| KKKKKKKKKKKKKKKK | 16 | 51 |
| KRKKRKKRKKRKKRKKRK | 18 | 52 |
| KRKKRKKRKKRKKRKKRKK | 19 | 53 |
| RRRRRRRRRRRRRRRRRRR | 19 | 54 |
| KKKKKKKKKKKKKKKKKKK | 19 | 55 |
| KRKKRKKRKRSKRKKRKKRK | 20 | 56 |
| KRKKRKKRKRSKRKKRKKRKK | 21 | 57 |
| KRKKRKKRKKRKKRKKRKKRK | 21 | 58 |
| KRKKRKKRKRGSGKRKKRKKRK | 22 | 59 |
| KRKKRKKRKRGSGSGKRKKRKKRK | 24 | 60 |
| KRKKRKKRKKRKKRKKRKRKKRKK | 25 | 61 |
| KRKKRKKRKRSKRKKRKKRKRSKRKKRKKRK | 31 | 62 |
| KRKKRKKRKRGSGSGKRKKRKKRKGSGSGKRKKRKKRK | 38 | 63 |
| KRKKRKKRKKRKKRKKRKKRKKRKKRKKRKKRKKRKKRK | 39 | 64 |
| KRKKRKKRKRSKRKKRKKRKRSKRKKRKKRKRSKRKKRKKRK | 42 | 65 |

In a further aspect of the present invention at least one of the additional amino acid sequence stretches is an antimicrobial peptide, which comprises a positive net charge and around 50% hydrophobic amino acids. The antimicrobial peptides are amphipathic with a length of about 12 to about 50 amino acid residues. The antimicrobial peptides are naturally occurring in insects, fish, plants, arachnids, vertebrates or mammals. Preferably the antimicrobial peptide may be naturally occurring in radish, silk moth, wolf spider, frog, preferably in *Xenopus laevis, Rana* frogs, more preferably in *Rana catesbeiana*, toad, preferably Asian toad *Bufo* bufo gargarizans, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human.

In another preferred embodiment of the present invention the antimicrobial amino acid sequence stretches consist of about 0% to about 5%, or about 0% to about 35%, or about 10% to about 35% or about 15% to about 45%, or about 20% to about 45% positively charged amino acid residues, in particular lysine and/or arginine residues and of about 50% to about 80%, or about 60% to about 80%, or about 55% to about 75%, or about 70% to about 90% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

In another preferred embodiment of the present invention the antimicrobial amino acid sequence stretches consist of about 4% to about 58% positively charged amino acid residues, in particular lysine and/or arginine residues and of about 33% to about 89% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

Examples for antimicrobial amino acid sequences which may be used in carrying out the present invention are listed in the following table.

TABLE 3

| Peptide | Sequence | SEQ ID NO |
|---|---|---|
| LL-37 | LLGDFFRKSKEKIGKEFKRIVQRIKDFLRNLVPRTES | 66 |
| SMAP-29 | RGLRRLGRKIAHGVKKYGPTVLRIIRIAG | 67 |
| Indolicidin | ILPWKWPWWPWRR | 68 |
| Protegrin | RGGRLCYCRRRFCVCVGR | 69 |
| Cecropin P1 | SWLSKTAKKLENSAKKRISEGIAIAIQGGPR | 70 |
| Magainin | GIGKFLHSAKKFGKAFVGEIMNS | 71 |
| Pleurocidin | GWGSFFKKAAHVGKHVGKAALTHYL | 72 |
| Cecropin A (A.aegypti) | GGLKKLGKKLEGAGKRVFNAAEKALPVVAGAKALRK | 73 |
| Cecropin A (D. melanogaster) | GWLKKIGKKIERVGQHTRDATIQGLGIPQQAANVAATARG | 74 |
| Buforin II | TRSSRAGLQFPVGRVHRLLRK | 75 |
| Sarcotoxin IA | GWLKKIGKKIERVGQHTRDATIQGLGIAQQAANVAATAR | 76 |
| Apidaecin | ANRPVYIPPPRPPHPRL | 77 |
| Ascaphine 5 | GIKDWIKGAAKKLIKTVASHIANQ | 78 |
| Nigrocine 2 | GLLSKVLGVGKKVLCGVSGLVC | 79 |
| Pseudin 1 | GLNTLKKVFQGLHEAIKLINNHVQ | 80 |
| Ranalexin | FLGGLIVPAMICAVTKKC | 81 |
| Melittin | GIGAVLKVLTTGLPALISWIKRKRQQ | 82 |
| Lycotoxin 1 | IWLTALKFLGKHAAKKLAKQQLSKL | 83 |
| Parasin 1 | KGRGKQGGKVRAKAKTRSS | 84 |
| Buforin I | AGRGKQGGKVRAKAKTRSSRAGLQFPVGRVHRLLRKGNY | 85 |
| Dermaseptin 1 | ALWKTMLKKLGTMALHAGKAALGAAADTISQGTQ | 86 |
| Bactenecin 1 | RLCRIVVIRVCR | 87 |
| Thanatin | GSKKPVPIIYCNRRTGKCQRM | 88 |
| Brevinin 1T | VNPIILGVLPKVCLITKKC | 89 |
| Ranateurin 1 | SMLSVLKNLGKVGLGFVACKINIKQC | 90 |
| Esculentin 1 | GIFSKLGRKKIKNLLISGLKNVGKEVGMDVVRTGIKIAGCKIKGEC | 91 |

TABLE 3-continued

| Peptide | Sequence | SEQ ID NO |
|---|---|---|
| Tachyplesin | RWCFRVCYRGICYRKCR | 92 |
| Androctonin | RSVCRQIKICRRRGGCYYKCTNRPY | 93 |
| alpha-defensin | DCYCRIPACIAGERRYGTCIYQGRLWAFCC | 94 |
| beta-defensin | NPVSCVRNKGICVPIRCPGSMKQIGTCVGRAVKCCRKK | 95 |
| theta-defensin | GFCRCLCRRGVCRCICTR | 96 |
| defensin (sapecin A) | ATCDLLSGTGINHSACAAHCLLRGNRGGYCNGKAVCVCRN | 97 |
| Thionin (crambin) | TTCCPSIVARSNFNVCRIPGTPEAICATYTGCIIIPGATCPGDYAN | 98 |
| defensin from radish | QKLCQRPSGTWSGVCGNNNACKNQCIRLEKARHGSCNYVFPAHCICYFPC | 99 |
| Drosomycin | DCLSGRYKGPCAVWDNETCRRVCKEEGRSSGHCSPSLKCWCEGC | 100 |
| Hepcidin | DTHFPICIFCCGCCHRSKCGMCCKT | 101 |
| Bac 5 | RFRPPIRRPPIRPPFYPPFRPPIRPPIFPPIRPPFRPPLGRPFP | 102 |
| PR-39 | RRRPRPPYLPRPRPPPFFPPRLPPRIPPGFPPRFPPRFP | 103 |
| Pyrrhocoricin | VDKGSYLPRPTPPRPIYNRN | 104 |
| Histatin 5 | DSHAKRHHGYKRKFHEKHHSHRGY | 105 |
| ECP19 | RPPQFTRAQWFAIQHISLN | 106 |
| MSI-594 | GIGKFLKKAKKGIGAVLKVLTTG | 107 |
| TL-ColM | METLTVHAPSPSTNLPSYGNGAFSLSAPHVPGAGP | 108 |
| SBO | KLKKIAQKIKNFFAKLVA | 109 |

In a further aspect of the present invention at least one of the additional amino acid sequence stretches may be a sushi peptide which is described by Ding J L, Li P, Ho B Cell Mol Life Sci. 2008 April; 65(7-8):1202-19. The Sushi peptides: structural characterization and mode of action against Gram-negative bacteria. Especially preferred is the sushi 1 peptide according to SEQ ID NO: 110.

Preferred sushi peptides are sushi peptides 51 and S3 and multiples thereof; FASEB J. 2000 Sep.; 14(12):1801-13.

In a further aspect of the present invention at least one of the additional amino acid sequence stretches is a hydrophobic peptide, which comprises at least 90% of the hydrophobic amino acid residues of valine, isoleucine, leucine, methionine, phenylalanine, tryptophan, cysteine, alanine, tyrosine, proline and/or glycine. In another preferred embodiment the hydrophobic peptide fused to the protein of the invention consists of about 90% to about 95%, or of about 90% to about 100%, or of about 95% to about 100% of the hydrophobic amino acid residues of valine, isoleucine, leucine, methionine, phenylalanine, tryptophan, cysteine, alanine, tyrosine, proline and/or glycine.

Preferred hydrophobic peptides are Walmagh1 having the amino acid sequence according to SEQ ID NO: 111 and the hydrophobic peptide having the amino acid sequence Phe-Phe-Val-Ala-Pro (SEQ ID NO: 112).

In a further aspect of the present invention at least one of the additional amino acid sequence stretches is an amphipathic peptide, which comprises one or more of the positively charged amino acid residues of lysine, arginine and/or histidine, combined to one or more of the hydrophobic amino acid residues of valine, isoleucine, leucine, methionine, phenylalanine, tryptophan, cysteine, alanine, tyrosine, proline and/or glycine. Side chains of the amino acid residues are oriented in order that cationic and hydrophobic surfaces are clustered at opposite sides of the peptide. Preferably, more than about 30, 40, 50, 60 or 70% of the amino acids in said peptide are positively charged amino acids. Preferably, more than about 30, 40, 50, 60 or 70%, of the amino acid residues in said peptide are hydrophobic amino acid residues. Advantageously, the amphipathic peptide is present at the N-terminal or the C-terminal end of the polypeptide according to the present invention.

In another embodiment of the invention, the amphipathic peptide consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or at least 50 amino acid residues. In a preferred embodiment at least about 30, 40, 50, 60 or 70% of said amino acid residues of the amphipathic peptide are either arginine or lysine residues and/or at least about 30, 40, 50, 60 or 70% of said amino acid residues of the amphipathic peptide are of the hydrophobic amino acids valine, isoleucine, leucine, methionine, phenylalanine, tryptophan, cysteine, alanine, tyrosine, proline and/or glycine.

In another preferred embodiment of the present invention the amphipathic peptide stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Preferred are amphipathic peptide stretches consisting of about 10% to about 50%, or about 20% to about 50%, or about 30% to about 45% or about 5% to about 30% positively charged amino acid residues, in particular lysine and/or arginine residues and of about 50% to about 85%, or about 50% to about 90%, or about 55% to about 90%, or about 60% to about 90%, or about 65% to about 90% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. In another preferred embodiment amphipathic peptide stretches consisting of 12% to about 50% positively charged amino acid residues, in particular lysine and/or arginine residues and of about 50% to about 85% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

Preferred amphipathic peptides are α4-helix of T4 lysozyme according to SEQ ID NO: 113 and WLBU2-Variant having the amino acid sequence according to SEQ ID NO: 114 and Walmagh 2 according to SEQ ID NO: 115.

The optional additional amino acid sequence stretches as specified above consist preferably of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred are those additional amino acid sequence stretches consisting of about 5 to about 100 amino acid residues, about 5 to about 50 or about 5 to about 30 amino acid residues. More preferred are peptide stretches consisting of about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues.

In a preferred embodiment the inventive polypeptide comprises at least one amino acid sequence stretch selected from the group consisting of KRK and SEQ ID NOs: 41-115.

An non-limiting example for a polypeptide according to the present invention comprising an additional amino acid sequence stretch is SEQ ID NO: 116, which comprises an N-terminal SMAP-29 peptide (SEQ ID NO: 67), a CBD deriving from KZ144 endolysin exhibiting 4 mutations (SEQ ID NO: 8) and a Lys68 endolysin sequence with a P78S mutation (SEQ ID NO: 26).

The additional amino acid sequence stretch of the polypeptide according to the present invention may be linked to the rest of the enzyme by intervening additional amino acid residues e.g. due to cloning reasons. Alternatively, the additional amino acid sequence stretches may be directly linked to the rest of the enzyme sequence without intervening linker sequences. The additional amino acid sequences, if more than one present in the inventive polypeptide and positioned on the same terminus of the enzyme, may likewise be linked to each other by additional intervening amino acid residues or may be directly joined to each other.

Preferably, said intervening additional amino acid residues may not be recognized and/or cleaved by proteases. Preferably said additional amino acid sequences are linked to each other and/or to the enzyme by at least 1, 2, 3, 4, 5, 6, 7, 8, 9 or 10 additional intervening amino acid residues.

In a preferred embodiment the at least one additional amino acid sequence stretch is linked to the rest of the inventive polypeptide, preferably at the N- or C-terminus of the polypeptide according to the present invention, by the additional intervening amino acid residues glycine, serine and serine (Gly-Ser-Ser), glycine, alanine, glycine and alanine (Gly-Ala-Gly-Ala; SEQ ID NO:117), glycine, alanine, glycine, alanine, glycine, alanine, glycine and alanine (Gly-Ala-Gly-Ala-Gly-Ala-Gly-Ala; SEQ ID NO:118) or glycine, alanine, glycine, alanine, glycine, alanine, glycine, alanine, glycine, alanine, glycine and alanine (Gly-Ala-Gly-Ala-Gly-Ala-Gly-Ala-Gly-Ala-Gly-Ala; SEQ ID NO:119).

Aside of the enzymatic domain (i.e. a domain having the activity of degrading the peptidoglycan of Gram-negative bacteria), the cell wall binding domain, and the optional additional amino acid sequence stretches, as defined herein, the inventive polypeptide may of course also comprise other amino acid sequence elements, e.g. one or more tags, e.g. a His-tag, Strep-tag, Avi-tag, Myc-tag, Gst-tag, JS-tag, cystein-tag, FLAG-tag or other tags known in the art, thioredoxin, maltose binding proteins (MBP) etc.

In this context, the inventive polypeptide, preferably having the ability of degrading the peptidoglycan layer of Gram negative bacteria, may additional comprise a tag e.g. for purification. Preferred is a $His_6$-tag (SEQ ID NO: 120), preferably at the C-terminus and/or the N-terminus of the polypeptide according to the present invention. Said tag can be linked to the polypeptide by additional amino acid residues e.g. due to cloning reasons. Preferably said tag can be linked to the protein by at least 1, 2, 3, 4, 5, 6, 7, 8, 9 or 10 additional amino acid residues. Preferably said additional amino acid residues may not be recognized and/or cleaved by proteases. In a preferred embodiment the inventive polypeptide comprises a $His_6$-tag at its C-terminus linked to the polypeptide by the additional amino acid residues lysine and glycine (Lys-Gly) or leucine and glutamic acid (Leu-Glu). Preferably, said additional amino acid residues may be not recognized or cleaved by proteases. In another preferred embodiment the inventive polypeptide comprises a $His_6$-tag at its N-terminus linked to the polypeptide by the additional amino acid residues lysine and glycine (Lys-Gly) or leucine and glutamic acid (Leu-Glu). In another preferred embodiment the polypeptide comprises a $His_6$-tag at its N- and C-terminus linked to the polypeptide by the additional amino acid residues lysine and glycine (Lys-Gly) or leucine and glutamic acid (Leu-Glu).

A polypeptide according to the present invention can be produced by standard means known in the art, e.g. by recombinant expression of nucleic acids encoding the respective polypeptide in appropriate host cells. If the inventive polypeptide comprises for example additionally amino acid sequence stretches or tags etc., such fusion proteins may be produced by linking the required individual nucleic acid sequences using standard cloning techniques as described e.g. by Sambrook et al. 2001, Molecular Cloning: A Laboratory Manual. Such a polypeptide may be produced likewise with methods known in the art, e.g., in recombinant DNA expression systems.

III. Nucleic Acids, Vectors, Bacteriophages and Host Cells

The present invention does also relate to nucleic acids encoding one or more inventive polypeptides of the present invention. The inventive nucleic acid may take all forms conceivable for a nucleic acid. In particular the nucleic acids according to the present invention may be RNA, DNA or hybrids thereof. They may be single-stranded or double-stranded. The may have the size of small transcripts or of entire genomes, such as a bacteriophage genome. As used herein, a nucleic acid encoding one or more inventive polypeptides of the present invention may be a nucleic acid reflecting the sense strand. Likewise, the antisense strand is also encompassed. The nucleic acid may encompass a heterologous promotor for expression of the inventive polypeptide.

In a further aspect the present invention relates to a vector comprising a nucleic acid according to the present invention. Such vector may for example be an expression vector allowing for expression of an inventive polypeptide. Said expression may be constitutive or inducible. The vector may also be a cloning vector comprising the nucleic acid sequence of the current invention for cloning purposes.

The present invention does also relate to a bacteriophage comprising an inventive nucleic acid, in particular comprising an inventive nucleic acid encoding a polypeptide according to the present invention.

The present invention does also relate to (isolated) host cells comprising a polypeptide, nucleic acid, vector, or bacteriophage according to the present invention. The host cells may be selected in particular from the group consisting of bacterial cells and yeast cells. Where appropriate, other suitable host cells may be immortalized cell lines, e.g. of mammalian (in particular human) origin. Particularly preferred host cells comprise a polypeptide according to the present invention.

IV. Compositions

In a further aspect the present invention relates to a composition comprising a polypeptide according to the present invention, a nucleic acid according to the present invention, a vector according to the present invention, a bacteriophage according to the present invention and/or a host cell according to the present invention.

A composition according to the present invention may be a pharmaceutical composition comprising a pharmaceutical acceptable diluent, excipient or carrier.

In an even further aspect the composition according to the present invention is a cosmetic composition. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the inventive polypeptide, nucleic acid, vector, host cell and/or composition in order to achieve a comedolytic effect.

V. Uses

In a further aspect the present invention relates to a polypeptide according to the present invention, a nucleic acid according to the present invention, a vector according to the present invention, a bacteriophage according to the present invention, a host cell according to the present invention, and/or a composition according to the present invention for use in a method of treatment of the human or animal body by surgery or therapy or in diagnostic methods practiced on the human or animal body. In such scenarios the antibacterial activity of polypeptide of the present invention can be exploited, in particular if the polypeptide comprises the additional amino acid sequence stretch specified above.

Such method typically comprises administering to a subject an effective amount of an inventive polypeptide, nucleic acid, vector, bacteriophage, host cell or a composition. The subject may for example be a human or an animal, with human subjects being more preferred. In particular, the inventive polypeptide, the inventive nucleic acid, the inventive vector, the inventive bacteriophage, the inventive host cell, and/or the inventive composition may be used in methods for the treatment or prevention of bacterial infections, such Gram-negative bacterial infections.

The dosage and route of administration used in a method of treatment (or prophylaxis) according to the present invention depends on the specific disease/site of infection to be treated. The route of administration may be for example oral, topical, nasopharyngeal, parenteral, intravenous, rectal or any other route of administration.

For application of an inventive polypeptide, nucleic acid, vector, bacteriophage, host cell or composition to a site of infection (or site endangered to be infected) a formulation may be used that protects the active compounds from environmental influences such as proteases, oxidation, immune response etc., until it reaches the site of infection. Therefore, the formulation may be capsule, dragee, pill, suppository, injectable solution or any other medical reasonable galenic formulation. Preferably, the galenic formulation may comprise suitable carriers, stabilizers, flavourings, buffers or other suitable reagents. For example, for topical application the formulation may be a lotion or plaster, for nasopharyngeal application the formulation may be saline solution to be applied via a spray to the nose.

Preferably, an inventive polypeptide, nucleic acid, vector, bacteriophage, host cell or composition is used in combination with other conventional antibacterial agents, such as antibiotics, lantibiotics, bacteriocins or endolysins, etc. The administration of the conventional antibacterial agent can occur prior to, concurrent with or subsequent to administration of the inventive polypeptide, nucleic acid, vector, bacteriophage, host cell or composition.

In a further aspect the present invention relates to the inventive polypeptide, nucleic acid, vector, bacteriophage, host cell or composition for use as diagnostic means in medical diagnostics, food diagnostics, feed diagnostics, or environmental diagnostics, in particular as a diagnostic means for the diagnostic of bacterial infection, in particular those caused by Gram-negative bacteria. In this respect the inventive polypeptide, nucleic acid, vector, host cell or composition may be used as a tool to specifically degrade the peptidoglycan of pathogenic bacteria, in particular of Gram-negative pathogenic bacteria. The degradation of the bacterial cells by the inventive polypeptide, nucleic acid, vector, host cell or composition can be supported by the addition of detergents like Triton X-100 or other additives which weaken the bacterial cell envelope like polymyxin B. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. β-galactosidase for enterobacteria, coagulase for coagulase positive strains).

In a further aspect the present invention relates to the use of the inventive polypeptide, the inventive nucleic acid, the inventive vector, the inventive bacteriophage, the inventive host cell, and/or the inventive composition, as an antimicrobial in food, feed, or cosmetics, or use as disinfecting agent. They can be used in particular for the treatment or prevention of Gram-negative bacterial contamination of foodstuff, of food processing equipment, of food processing plants, of (inanimate) surfaces coming into contact with foodstuff (such as shelves and food deposit areas), of feedstuff, of feed processing equipment, of feed processing plants, of (inanimate) surfaces coming into contact with feedstuff (such as shelves and feed deposit areas), of medical devices, or of (inanimate) surfaces in hospitals, doctor's offices and other medical facilities.

BRIEF DESCRIPTION OF THE FIGURES

In the following a brief description of the appended figures will be given. The figures are intended to illustrate the present invention in more detail. However, they are not intended to limit the scope of the invention to these specific examples.

VI. EXAMPLES

In the following, specific examples illustrating various embodiments and aspects of the invention are presented.

However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1: Variants of Lys68 Endolysin Having an Additional Gram-Negative CBD Exhibit Increased Muralytic Activity Two variants of *Salmonella* phage endolysin Lys68 were generated. The first variant is a fusion with a sequence comprising the CBD of EL188 endolysin (SEQ ID NO:12). The resulting chimeric variant cEL188-Lys68 comprises SEQ ID NO:29. The second variant is a fusion with the CBD of KZ144 endolysin (SEQ ID NO:7) The CBD used exhibits three point mutations in the sequence of the KZ144 CBD in which cysteine residues were replaced by serine residues. The resulting chimeric variant cKZ144-Lys68 comprises SEQ ID NO:30. The wildtype endolysin and its chimeric variants were expressed in *E. coli*. Subsequently, the proteins were purified. In order to test the muralytic activity of the enzymes, *Pseudomonas aeruginosa* PAO1 cells were treated with chloroform to remove the outer membrane. Therefore, 20 mM HEPES pH 7.4, 150 mM NaCl buffer was saturated with chloroform. Exponentially growing *P. aeruginosa* cells were harvested and resuspended in chloroform buffer and incubated for 45 minutes. Afterwards, the cells were washed two times in 20 mM HEPES pH 7.4 and 150 mM NaCl and subsequently diluted with the same buffer to a final OD600 of about 0.8. Subsequently, each protein was added at a final concentration of 0.005 µM to an aliquot of 1 ml cell solution and the reduction of the OD600 was recorded over a period of 1800 seconds.

Figure 1:
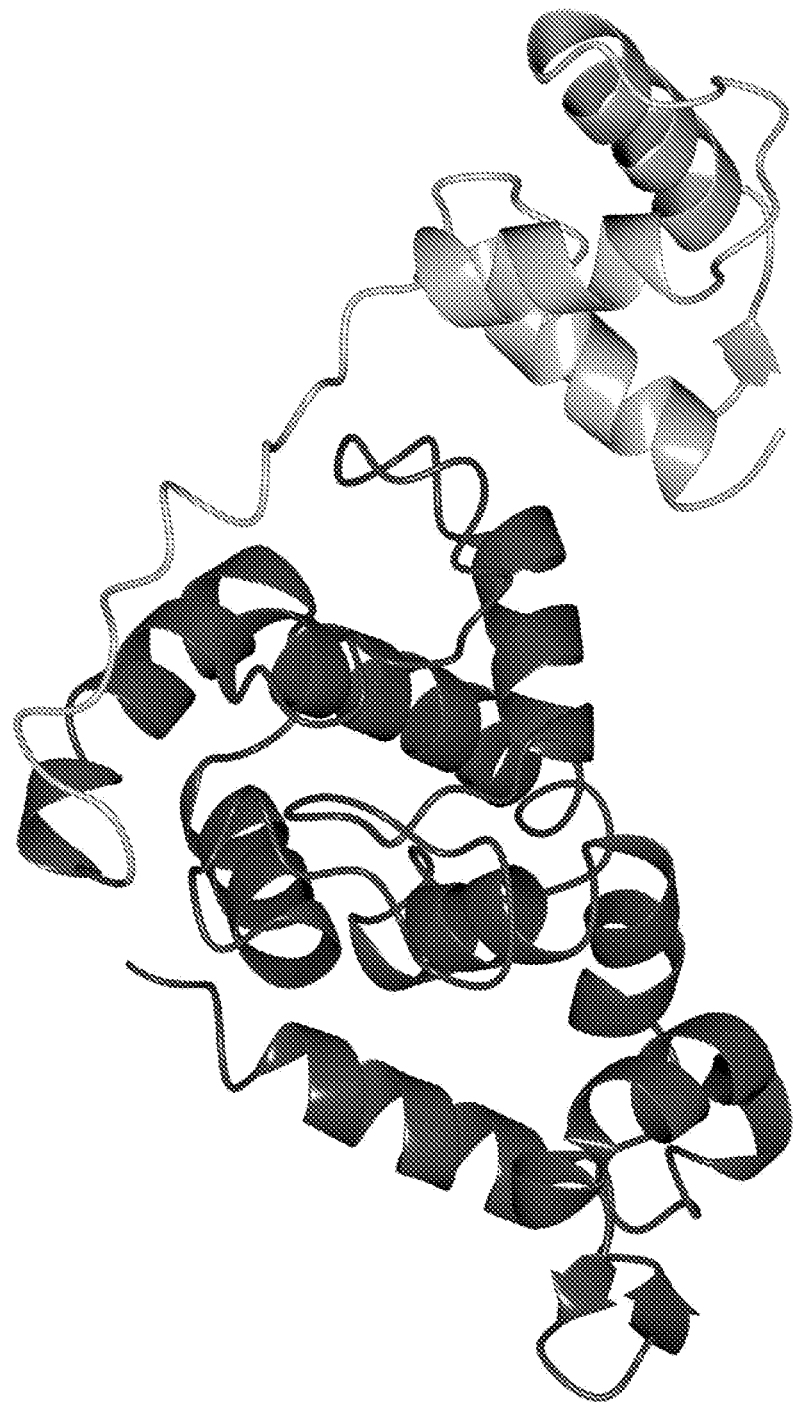
FIG. 1: illustrates an archetypical structure of a Gram-negative modular endolysin. Depicted is the 3D structure of KZ 144 endolysin (Fokine et al. J. Biol. Chem. 2008, 283:7242-7250). The cell wall binding domain (CBD) is a domain (see top of Fig) clearly separate from the enzymatically acitve domain (bottom of structure).
Figure 2:
FIG. 2: illustrates the structure of a Gram-negative globular endolysin. Depicted is the modelled 3D structure of Lys394 endolysin. The structure has been generated by way of homologxy modeling on basis of the structure of T5 lysozyme, which shares a 97% sequence identity with Lys394. A domain architecture, as can be seen for, e.g. KZ 144 endolysin, can not be found in the structure of Lys394 endolysin.
Figure 3:
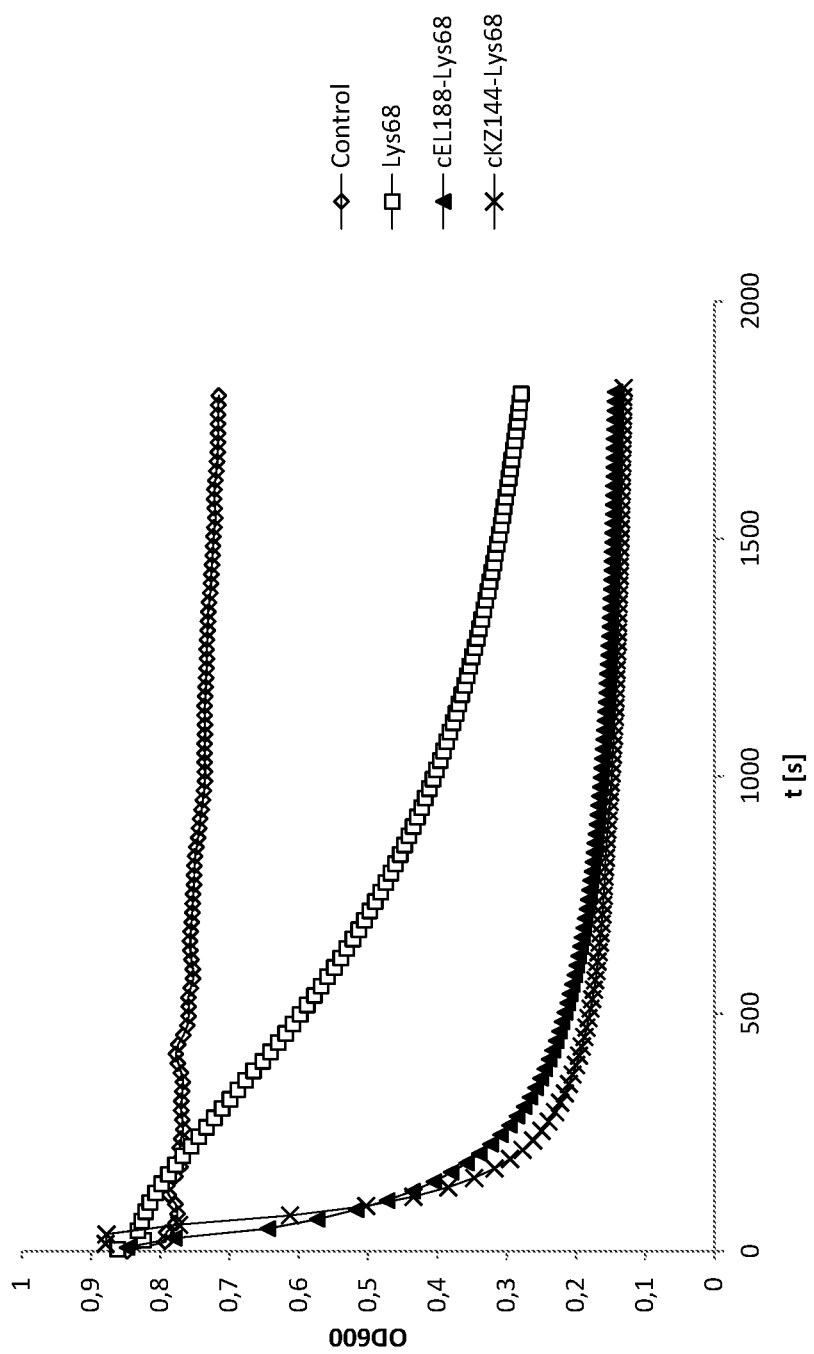
FIG. 3: illustrates muralytic activity for *Salmonella* phage endolysin Lys68 and two chimeric variants thereof (cEL188-Lys68; cKZ144-Lys68) on chloroform treated *P. aeruginosa* cells. The fusion proteins exhibiting the additional heterologous CBD show increased activity.
Figure 4:
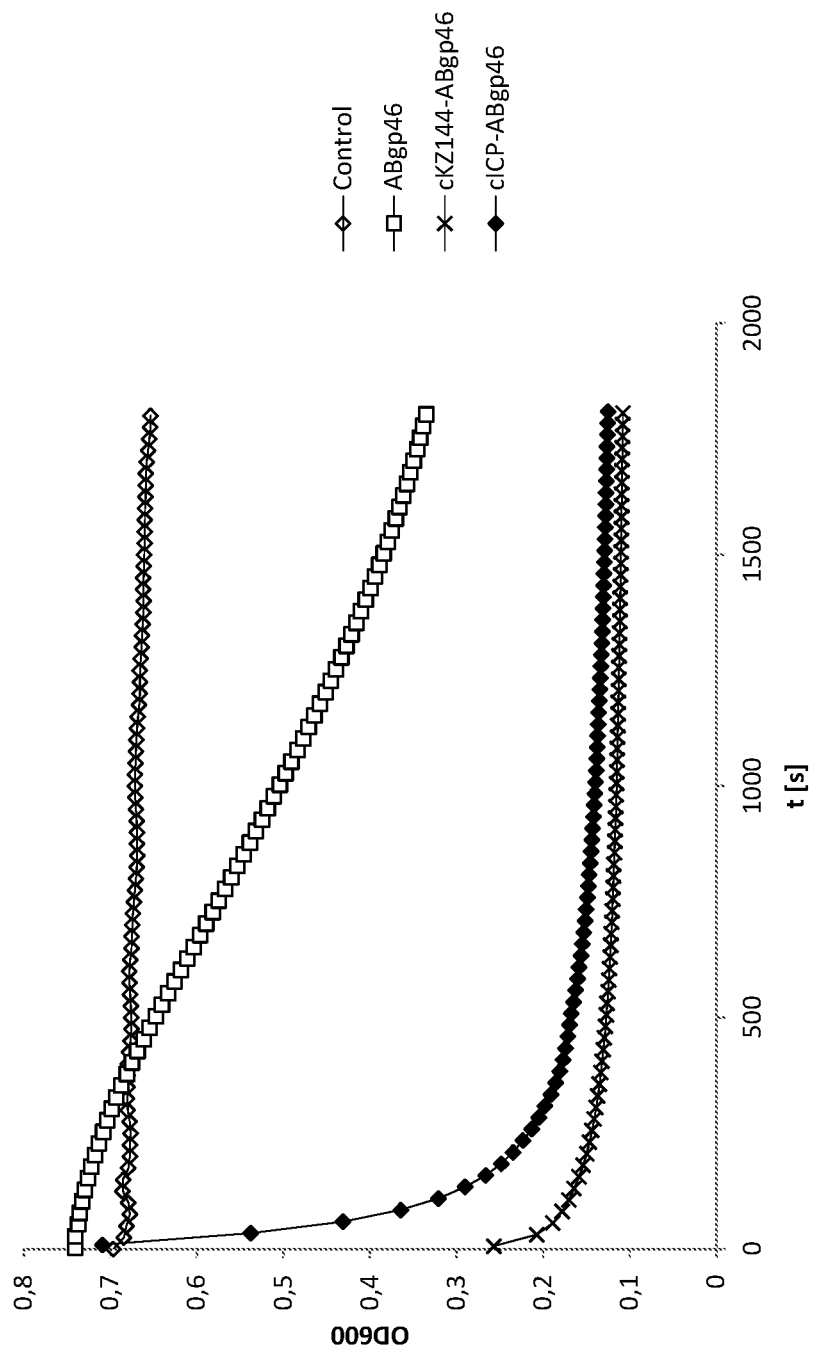
FIG. 4: illustrates muralytic activity for ABgp46 endolysin and two chimeric variants thereof (cKZ144-ABgp46; cICP-ABgp46) on chloroform treated *P. aeruginosa* cells. The fusion proteins exhibiting the additional heterologous CBD show increased activity.

The two chimeric variants of Lys68 endolysin having an additional Gram-negative CBD exhibit significantly increased muralytic activity in comparison to the wildtype endolysin (see FIG. 3).

Example 2: Variants of ABgp46 Endolysin Having an Additional Gram-Negative CBD Exhibit Increased Muralytic Activity Two variants of ABgp46 endolysin (deriving from *Acinetobacter* phage vB_AbaP_CEB1) were generated. The first variant is a fusion with the CBD of KZ144 endolysin (SEQ ID NO: 7). The resulting chimeric variant cKZ144-ABgp46 comprises SEQ ID NO:31. The second variant is a fusion with the CBD of the baseplate tail protein of *Vibrio* phage ICP1 (SEQ ID NO:14). The resulting chimeric variant cICP-ABgp46 comprises SEQ ID NO:32. The wildtype endolysin and its chimeric variants were expressed in *E. coli*. Subsequently, the proteins were purified. In order to test the muralytic activity of the enzymes, *Pseudomonas aeruginosa* PAO1 cells were treated with chloroform to remove the outer membrane. Therefore, 20 mM HEPES pH 7.4, 150 mM NaCl buffer was saturated with chloroform. Exponentially growing *P. aeruginosa* cells were harvested and resuspended in chloroform buffer and incubated for 45 minutes. Afterwards, the cells were washed two times in 20 mM HEPES pH 7.4 and 150 mM NaCl and subsequently diluted with the same buffer to a final OD600 of about 0.8. Subsequently, each protein was added at a final concentration of 0.005 µM to an aliquot of 1 ml cell solution and the reduction of the OD600 was recorded over a period of 1800 seconds.

Figure 5:
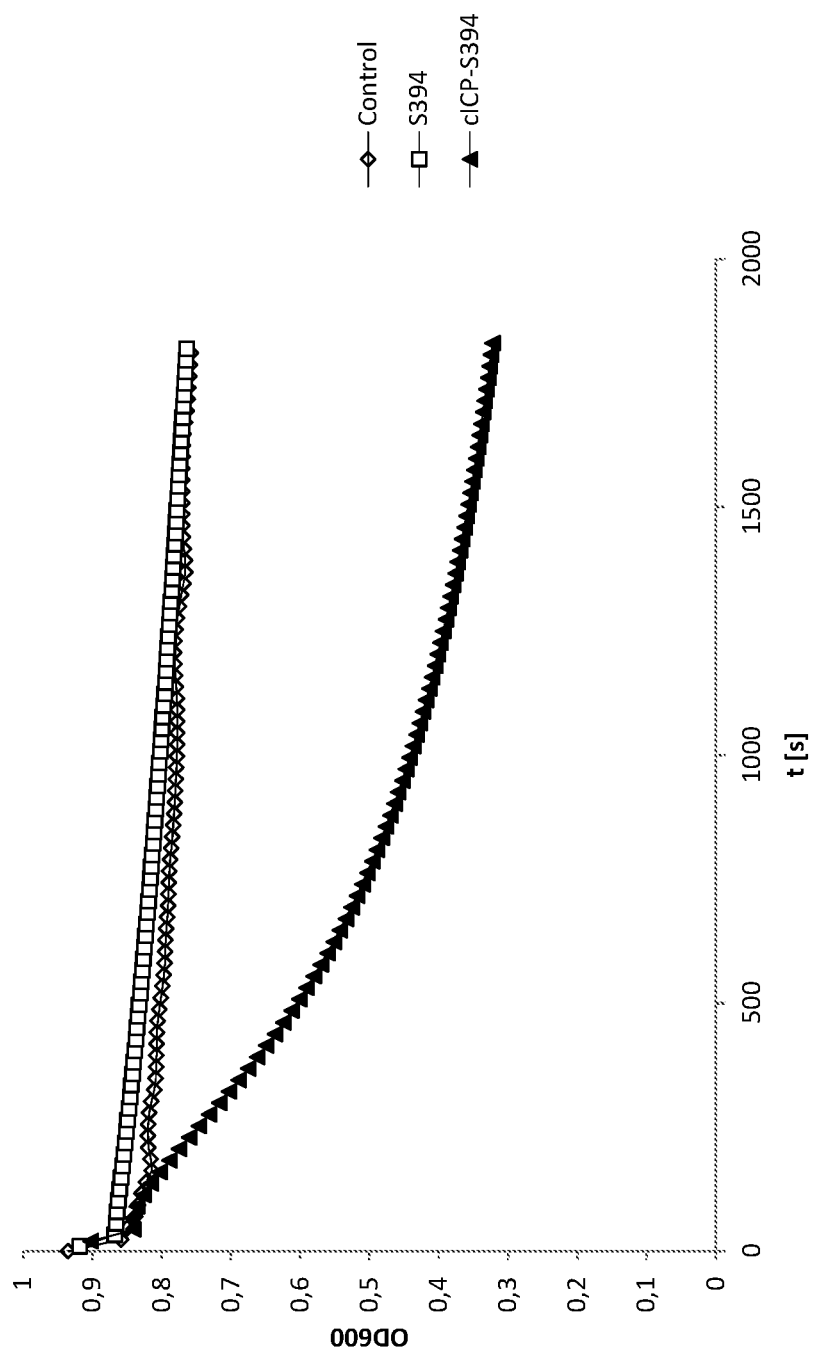
FIG. 5: illustrates muralytic activity for Lys394 endolysin and a chimeric variant thereof (cICP-5394) on chloroform treated *P. aeruginosa* cells. The fusion protein exhibiting the additional heterologous CBD shows increased activity.

The two chimeric variants of ABgp46 endolysin having an additional Gram-negative CBD exhibit significantly increased muralytic activity in comparison to the wildtype endolysin (see FIG. 5).

Example 3: Variant of Lys394 Endolysin Having an Additional CBD Exhibits De Novo Muralytic Activity on P-Aeroguinosa A variant of *Salmonella* phage endolysin Lys394 was generated. The variant is a fusion with the CBD of ICP tail/baseplate protein (SEQ ID NO: 14). The resulting chimeric variant comprises SEQ ID NO:33. The wildtype endolysin and its chimeric variant were expressed in *E. coli*. Subsequently, the proteins were purified. In order to test the muralytic activity of the enzymes, *Pseudomonas aeruginosa* PAO1 cells were treated with chloroform to remove the outer membrane. Therefore, 20 mM HEPES pH 7.4, 150 mM NaCl buffer was saturated with chloroform. Exponentially growing *P. aeruginosa* cells were harvested and resuspended in chloroform buffer and incubated for 45 minutes. Afterwards, the cells were washed two times in 20 mM HEPES pH 7.4 and 150 mM NaCl and subsequently diluted with the same buffer to a final OD600 of about 0.8. Subsequently, each protein was added at a final concentration of 0.005 µM to an aliquot of 1 ml cell solution and the reduction of the OD600 was recorded over a period of 1800 seconds.

In contrast to the wildtype endolysin, the chimeric variant of Lys394 endolysin exhibits significant muralytic activity on *P. aeruginosa* cells (see FIG. 6) already at a concentration of 0.005 µM.

Example 4: Fusion Protein Exhibiting Lys68 Endolysin Variant, a CBD Variant of the KZ144 Endolysin CBD and an Additional Antimicrobial Peptide SMAP-29 Exhibits Antibacterial Activity Against a Broad Range of Gram-Negative Bacteria In a further experiment compatibility of a chimeric endolysin according to the present invention with an antimicrobial peptide to effectively kill Gram-negative bacteria was tested. For this purpose, a fusion protein was generated which comprises the components SMAP-29 (SEQ ID NO: 67), a derivative of the KZ144 CBD exhibiting four mutations (SEQ ID NO: 8) and a derivative of Lys68 endolysin (SEQ ID NO: 26). The resulting polypeptide comprises the consecutive sequence of SEQ ID NO: 116. Due to the mutations in SEQ ID NO: 8 and 26, the resulting fusion protein exhibited improved thermal stability. The chimeric variant was expressed in *E. coli*.

Briefly, bacteria were grown in (Luria-Bertani) medium and diluted 1:10 in Mueller-Hinton medium. At optical density $OD_{600}$ of about 0.6 bacteria were diluted in the same medium 1:10 followed by a 1:500 dilution. Protein buffer (20 mM HEPES, 500 mM NaCl, pH 7.4) and proteins were pipetted into a 96 well plate, using different concentrations of proteins and an end volume of 20 µl including 500 µM EDTA final concentration (if required). 180 µl of bacterial cells or a medium (Mueller-Hinton) control were given to the 96 well plate and mixed. The plate was incubated for 18-22 hours at 37° C. and the bacterial growth was determined measuring the OD600 values of the wells. The MIC which is the protein concentration of the well which showed the same OD600 value as the no-bacteria control was determined.

The fusion protein showed antibacterial activity against a surprisingly broad range of Gram-negative bacteria including *Pseudomonas*, *Klebsiella*, *Escherichia*, *Acinetobacter* and *Salmonella* species. The corresponding results are described in table 4.

TABLE 4

MIC values

| Bacterial strain | EDTA | MIC (µg/ml) |
|---|---|---|
| S2 *Pseudomonas aeruginosa* Br667 | 0.5 mM | 10 |
| S84 *Pseudomonas aeruginosa* Aa249 | 0.5 mM | 10 |
| S53 *Klebsiella pneumoniae* B10-03.05.700 | 0.5 mM | 20 |
| S516 *Klebsiella pneumoniae* va32842 | 0.5 mM | 17.5 |
| S441 *Escherichia coli* B12-11.20.0192 | 0.5 mM | 5 |
| S458 *Escherichia coli* B12-11.30.0188 | 0.5 mM | 5 |
| S45 *Acinetobacter baumannii* 2671 | 0.0 mM | 10 |
| S138 *Acinetobacter baumannii* NRZ-00066 | 0.0 mM | 10 |
| S795 *Salmonella Enteritidis* LGL-238 | 0.5 mM | 7.5 |
| S25 *Salmonella Thyphimurium* DSM 17058 | 0.5 mM | 15 |

In addition, the fusion protein comprising SEQ ID NO: 116 exhibited significant thermal stability due to the mutations K59M and P78S in the sequence of Lys68 endolysin.

The invention claimed is:

1. A polypeptide comprising the amino acid sequence of a globular Gram-negative endolysin and the amino acid sequence of a cell wall binding domain of i) a modular Gram-negative endolysin or ii) a bacteriophage tail/baseplate protein, wherein said polypeptide comprises an amino acid sequence having at least 80% sequence identity to an amino acid sequence selected from the group consisting of SEQ ID NOs: 29, 30, 31, 32, 33, 34, 35, 36, 37, 38, 39 and 40, and has muralytic activity.

2. The polypeptide according to claim 1, wherein the Gram-negative modular endolysin is selected from the group consisting of KZ144, EL188, OBPgpLYS, PVPSE1gp146, and 201φ2-1 endolysin.

3. The polypeptide according to claim 1, wherein the bacteriophage tail/baseplate protein is a bacteriophage tail/baseplate protein of a bacteriophage selected from the group consisting of *Vibrio* phage ICP1 and *Vibrio* phage RYC.

4. The polypeptide according to claim 1, wherein the globular endolysin is selected from the group consisting of Lys68, ABgp46 and Lys394 endolysin.

5. The polypeptide according to claim 1, wherein the polypeptide does not comprise the amino acid sequence of a Gram-negative modular endolysin.

6. The polypeptide according to claim 1, wherein the polypeptide does not comprise an enzymatically active domain (EAD) of a Gram-negative modular endolysin.

7. The polypeptide according to claim 1, wherein the enzymatic activity of the globular endolysin is the only enzymatic activity of the polypeptide.

8. The polypeptide according to claim 1, wherein the amino acid sequence of the globular endolysin and the amino acid sequence of the cell wall binding domain are either linked directly to each other or via an intermediate linker sequence, wherein the linker sequence does not exceed more than 50 amino acids in length.

9. The polypeptide according to claim 1, wherein the polypeptide degrades peptidoglycan of at least one Gram-negative bacterial species.

10. The polypeptide according to claim 1, wherein the polypeptide binds to peptidoglycan of at least one Gram-negative bacterial species.

11. The polypeptide according to claim 1, wherein the polypeptide comprises an amino acid sequence selected from the group of sequences consisting of SEQ ID NOs: 29, 30, 31, 32, 33, 34, 35, 36, 37, 38, 39 and 40.

12. The polypeptide according to claim 1, wherein the polypeptide comprises additionally at least one amino acid sequence selected from the group consisting of amphipathic peptide, cationic peptide, polycationic peptide, hydrophobic peptide, naturally occurring antimicrobial peptide, sushi peptide and defensin.

13. The polypeptide according to claim 12, wherein the polypeptide comprises at least one additional amino acid sequence stretch selected from the group consisting of: KRK and SEQ ID NOs: 41-115.

14. The polypeptide according to claim 12, wherein the polypeptide comprises the amino acid sequence of SEQ ID NO: 116.

15. A method for treatment of the human or animal body, wherein the method comprises administering an efficient amount of the polypeptide according to claim 1, a nucleic acid or a vector encoding the polypeptide, or a host cell expressing the polypeptide.

16. The method according to claim 15, wherein the method is a method for preventing or treating bacterial infection of the human or animal body.

* * * * *

SEQUENCE LISTING

```
<160> NUMBER OF SEQ ID NOS: 120

<210> SEQ ID NO 1
<211> LENGTH: 61
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE
<222> LOCATION: (1)..(1)
<223> OTHER INFORMATION: Xaa can be any naturally occurring amino acid
      or absent; in particular it can be methionine
<220> FEATURE:
<221> NAME/KEY: MISC_FEATURE
<222> LOCATION: (6)..(6)
<223> OTHER INFORMATION: Xaa can be any naturally occurring amino acid,
      in particular cysteine, serine, arginine or aspargine, preferably
      serine, arginine or aspargine, most preferaby serine
```

```
<220> FEATURE:
<221> NAME/KEY: MISC_FEATURE
<222> LOCATION: (15)..(15)
<223> OTHER INFORMATION: Xaa can be any naturally occurring amino acid,
      in particular cysteine, serine, arginine or aspargine, preferably
      serine, arginine or aspargine, most preferaby serine
<220> FEATURE:
<221> NAME/KEY: MISC_FEATURE
<222> LOCATION: (42)..(42)
<223> OTHER INFORMATION: Xaa can be any naturally occurring amino acid,
      in particular cysteine, serine, arginine or aspargine, preferably
      serine, arginine or aspargine, most preferaby serine
<220> FEATURE:
<221> NAME/KEY: MISC_FEATURE
<222> LOCATION: (51)..(51)
<223> OTHER INFORMATION: Xaa can be any naturally occurring amino acid,
      in particular lysine or methionine

<400> SEQUENCE: 1

Arg Gly Asp Glu Val Xaa Gln Leu Gln Thr Leu Leu Asn Leu Xaa Gly
1               5                   10                  15

Tyr Asp Val Gly Lys Pro Asp Gly Ile Phe Gly Asn Asn Thr Phe Asn
            20                  25                  30

Gln Val Val Lys Phe Gln Lys Asp Asn Xaa Leu Asp Ser Asp Gly Ile
        35                  40                  45

Val Gly Xaa Asn Thr Trp Ala Glu Leu Phe Ser Lys Tyr
    50                  55                  60

<210> SEQ ID NO 2
<211> LENGTH: 70
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE
<222> LOCATION: (1)..(1)
<223> OTHER INFORMATION: Xaa can be any naturally occurring amino acid
      or absent; in particular it can be methionine
<220> FEATURE:
<221> NAME/KEY: MISC_FEATURE
<222> LOCATION: (14)..(14)
<223> OTHER INFORMATION: Xaa can be any naturally occurring amino acid,
      in particular cysteine, serine, arginine or aspargine, preferably
      serine, arginine or aspargine, most preferaby serine
<220> FEATURE:
<221> NAME/KEY: MISC_FEATURE
<222> LOCATION: (23)..(23)
<223> OTHER INFORMATION: Xaa can be any naturally occurring amino acid,
      in particular cysteine, serine, arginine or aspargine, preferably
      serine, arginine or aspargine, most preferaby serine
<220> FEATURE:
<221> NAME/KEY: MISC_FEATURE
<222> LOCATION: (50)..(50)
<223> OTHER INFORMATION: Xaa can be any naturally occurring amino acid,
      in particular cysteine, serine, arginine or aspargine, preferably
      serine, arginine or aspargine, most preferaby serine
<220> FEATURE:
<221> NAME/KEY: MISC_FEATURE
<222> LOCATION: (59)..(59)
<223> OTHER INFORMATION: Xaa can be any naturally occurring amino acid,
      in particular lysine or methionine

<400> SEQUENCE: 2

Xaa Lys Val Leu Arg Lys Gly Asp Arg Gly Asp Glu Val Xaa Gln Leu
1               5                   10                  15

Gln Thr Leu Leu Asn Leu Xaa Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45
```

```
Asn Xaa Leu Asp Ser Asp Gly Ile Val Gly Xaa Asn Thr Trp Ala Glu
 50                  55                  60
Leu Phe Ser Lys Tyr Ser
 65                  70
```

<210> SEQ ID NO 3
<211> LENGTH: 61
<212> TYPE: PRT
<213> ORGANISM: unknown
<220> FEATURE:
<223> OTHER INFORMATION: CBD of phiKZgp144

<400> SEQUENCE: 3

```
Arg Gly Asp Glu Val Cys Gln Leu Gln Thr Leu Leu Asn Leu Cys Gly
 1               5                  10                  15
Tyr Asp Val Gly Lys Pro Asp Gly Ile Phe Gly Asn Asn Thr Phe Asn
                 20                  25                  30
Gln Val Val Lys Phe Gln Lys Asp Asn Cys Leu Asp Ser Asp Gly Ile
             35                  40                  45
Val Gly Lys Asn Thr Trp Ala Glu Leu Phe Ser Lys Tyr
         50                  55                  60
```

<210> SEQ ID NO 4
<211> LENGTH: 61
<212> TYPE: PRT
<213> ORGANISM: Artificial sequence
<220> FEATURE:
<223> OTHER INFORMATION: Amino acids 9 to 69 of endolysin KZ144 (CBD)
      with three cysteines replaced by serine

<400> SEQUENCE: 4

```
Arg Gly Asp Glu Val Ser Gln Leu Gln Thr Leu Leu Asn Leu Ser Gly
 1               5                  10                  15
Tyr Asp Val Gly Lys Pro Asp Gly Ile Phe Gly Asn Asn Thr Phe Asn
                 20                  25                  30
Gln Val Val Lys Phe Gln Lys Asp Asn Ser Leu Asp Ser Asp Gly Ile
             35                  40                  45
Val Gly Lys Asn Thr Trp Ala Glu Leu Phe Ser Lys Tyr
         50                  55                  60
```

<210> SEQ ID NO 5
<211> LENGTH: 61
<212> TYPE: PRT
<213> ORGANISM: Artificial sequence
<220> FEATURE:
<223> OTHER INFORMATION: Amino acids 9 to 69 of endolysin KZ144 (CBD)
      with three cysteines replaced by serine and one lysine replaced by
      methionine

<400> SEQUENCE: 5

```
Arg Gly Asp Glu Val Ser Gln Leu Gln Thr Leu Leu Asn Leu Ser Gly
 1               5                  10                  15
Tyr Asp Val Gly Lys Pro Asp Gly Ile Phe Gly Asn Asn Thr Phe Asn
                 20                  25                  30
Gln Val Val Lys Phe Gln Lys Asp Asn Ser Leu Asp Ser Asp Gly Ile
             35                  40                  45
Val Gly Met Asn Thr Trp Ala Glu Leu Phe Ser Lys Tyr
         50                  55                  60
```

<210> SEQ ID NO 6
<211> LENGTH: 69
<212> TYPE: PRT

<213> ORGANISM: unknown
<220> FEATURE:
<223> OTHER INFORMATION: N-terminus incl. CBD of phiKZgp144 (aa 2-70)

<400> SEQUENCE: 6

Lys Val Leu Arg Lys Gly Asp Arg Gly Asp Glu Val Cys Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Cys Leu Asp Ser Asp Gly Ile Val Gly Lys Asn Thr Trp Ala Glu Leu
    50                  55                  60

Phe Ser Lys Tyr Ser
65

<210> SEQ ID NO 7
<211> LENGTH: 69
<212> TYPE: PRT
<213> ORGANISM: Artificial sequence
<220> FEATURE:
<223> OTHER INFORMATION: Amino acids 2 to 70 of endolysin KZ144 with
      three cysteines replaced by serine

<400> SEQUENCE: 7

Lys Val Leu Arg Lys Gly Asp Arg Gly Asp Glu Val Ser Gln Leu Gln
1               5                   10                  15

Thr Leu Leu Asn Leu Ser Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
    50                  55                  60

Phe Ser Lys Tyr Ser
65

<210> SEQ ID NO 8
<211> LENGTH: 69
<212> TYPE: PRT
<213> ORGANISM: Artificial sequence
<220> FEATURE:
<223> OTHER INFORMATION: Amino acids 2 to 70 of endolysin KZ144 with
      three cysteines replaced by serine and one lysine replaced by
      methionine

<400> SEQUENCE: 8

Lys Val Leu Arg Lys Gly Asp Arg Gly Asp Glu Val Ser Gln Leu Gln
1               5                   10                  15

Thr Leu Leu Asn Leu Ser Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Met Asn Thr Trp Ala Glu Leu
    50                  55                  60

Phe Ser Lys Tyr Ser
65

<210> SEQ ID NO 9
<211> LENGTH: 91
<212> TYPE: PRT
<213> ORGANISM: Artificial sequence

```
<220> FEATURE:
<223> OTHER INFORMATION: Consensus Sequence
<220> FEATURE:
<221> NAME/KEY: MISC_FEATURE
<222> LOCATION: (40)..(40)
<223> OTHER INFORMATION: Xaa can be any naturally occurring amino acid;
      in particular it can be glycine or tryptophan

<400> SEQUENCE: 9

Thr Lys Asn Gly Tyr Arg Asp Leu Gln Ala Leu Val Lys Glu Leu Gly
1               5                   10                  15

Leu Tyr Thr Gly Gln Ile Asp Gly Val Trp Gly Lys Gly Thr Ser Ser
            20                  25                  30

Ser Thr Glu Thr Leu Leu Arg Xaa Tyr Ala Glu Val Val Gly Lys Asn
        35                  40                  45

Thr Gly Gly Ile Gly Leu Pro Thr Thr Ser Asp Ala Ser Gly Tyr Asn
    50                  55                  60

Val Ile Thr Ala Leu Gln Arg Asn Leu Ala Phe Leu Gly Leu Tyr Ser
65                  70                  75                  80

Leu Thr Val Asp Gly Ile Trp Gly Asn Gly Thr
                85                  90

<210> SEQ ID NO 10
<211> LENGTH: 91
<212> TYPE: PRT
<213> ORGANISM: Unknown
<220> FEATURE:
<223> OTHER INFORMATION: ELgp188

<400> SEQUENCE: 10

Thr Lys Asn Gly Tyr Arg Asp Leu Gln Ala Leu Val Lys Glu Leu Gly
1               5                   10                  15

Leu Tyr Thr Gly Gln Ile Asp Gly Val Trp Gly Lys Gly Thr Ser Ser
            20                  25                  30

Ser Thr Glu Thr Leu Leu Arg Gly Tyr Ala Glu Val Val Gly Lys Asn
        35                  40                  45

Thr Gly Gly Ile Gly Leu Pro Thr Thr Ser Asp Ala Ser Gly Tyr Asn
    50                  55                  60

Val Ile Thr Ala Leu Gln Arg Asn Leu Ala Phe Leu Gly Leu Tyr Ser
65                  70                  75                  80

Leu Thr Val Asp Gly Ile Trp Gly Asn Gly Thr
                85                  90

<210> SEQ ID NO 11
<211> LENGTH: 91
<212> TYPE: PRT
<213> ORGANISM: Unknown
<220> FEATURE:
<223> OTHER INFORMATION: ELgp188

<400> SEQUENCE: 11

Thr Lys Asn Gly Tyr Arg Asp Leu Gln Ala Leu Val Lys Glu Leu Gly
1               5                   10                  15

Leu Tyr Thr Gly Gln Ile Asp Gly Val Trp Gly Lys Gly Thr Ser Ser
            20                  25                  30

Ser Thr Glu Thr Leu Leu Arg Trp Tyr Ala Glu Val Val Gly Lys Asn
        35                  40                  45

Thr Gly Gly Ile Gly Leu Pro Thr Thr Ser Asp Ala Ser Gly Tyr Asn
    50                  55                  60

Val Ile Thr Ala Leu Gln Arg Asn Leu Ala Phe Leu Gly Leu Tyr Ser
```

```
65                  70                  75                  80

Leu Thr Val Asp Gly Ile Trp Gly Asn Gly Thr
                85                  90

<210> SEQ ID NO 12
<211> LENGTH: 113
<212> TYPE: PRT
<213> ORGANISM: Unknown
<220> FEATURE:
<223> OTHER INFORMATION: ELgp188

<400> SEQUENCE: 12

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
                20                  25                  30

Thr Ser Ser Thr Glu Thr Leu Leu Arg Gly Tyr Ala Glu Val Val
            35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr

<210> SEQ ID NO 13
<211> LENGTH: 113
<212> TYPE: PRT
<213> ORGANISM: Unknown
<220> FEATURE:
<223> OTHER INFORMATION: WP_050469949.1 2-114

<400> SEQUENCE: 13

Asn Phe Arg Thr Lys Asn Gly Tyr Arg Asp Leu Gln Ala Leu Val Lys
1               5                   10                  15

Glu Leu Gly Leu Tyr Thr Gly Gln Ile Asp Gly Val Trp Gly Lys Gly
                20                  25                  30

Thr Ser Ser Thr Glu Thr Leu Leu Arg Trp Tyr Ala Glu Val Val
            35                  40                  45

Gly Lys Asn Thr Gly Gly Ile Gly Leu Pro Thr Thr Ser Asp Ala Ser
    50                  55                  60

Gly Tyr Asn Val Ile Thr Ala Leu Gln Arg Asn Leu Ala Phe Leu Gly
65                  70                  75                  80

Leu Tyr Ser Leu Thr Val Asp Gly Ile Trp Gly Asn Gly Thr Leu Ser
                85                  90                  95

Gly Leu Asp Lys Ala Phe Glu Val Tyr Lys Glu Arg Tyr Arg Thr Pro
            100                 105                 110

Thr

<210> SEQ ID NO 14
<211> LENGTH: 78
<212> TYPE: PRT
<213> ORGANISM: unknown
<220> FEATURE:
<223> OTHER INFORMATION: CBD of  tail baseplate protein of Vibrio phage
      ICP1
```

<400> SEQUENCE: 14

Ile Leu Lys Arg Gly Ser Ser Gly Ala Asp Val Lys Asn Met Gln Glu
1               5                   10                  15

Tyr Leu Thr Ala Leu Gly Tyr Asp Thr Lys Gly Val Glu Gly Thr Phe
            20                  25                  30

Glu Gly Gly Thr Glu Ser Ala Val Lys Ala Phe Gln Lys Asp Met Ser
        35                  40                  45

Phe Thr Val Val Asp Gly Ile Gly Asn Gln Thr Ala Lys His Leu
    50                  55                  60

Val Asp Met Tyr Tyr Gly Lys Val Val Pro Phe Gly Tyr Val
65                  70                  75

<210> SEQ ID NO 15
<211> LENGTH: 111
<212> TYPE: PRT
<213> ORGANISM: unknown
<220> FEATURE:
<223> OTHER INFORMATION: CBD of OBPgpLYS endolysin

<400> SEQUENCE: 15

Asn Ala Ser Ile Ile Met Ser Ile Gln Arg Thr Leu Ala Ser Leu Ser
1               5                   10                  15

Leu Tyr Gly Gly Arg Ile Asp Gly Leu Phe Gly Glu Lys Cys Arg Gly
            20                  25                  30

Ala Ile Ile Leu Met Leu Asn Lys Val Tyr Pro Asn Phe Ser Thr Asn
        35                  40                  45

Lys Leu Pro Ser Asn Thr Tyr Glu Ala Glu Ser Val Phe Thr Phe Leu
    50                  55                  60

Gln Thr Ala Leu Ala Gly Val Gly Leu Tyr Thr Ile Thr Ile Asp Gly
65                  70                  75                  80

Lys Trp Gly Gly Thr Ser Gln Gly Ala Ile Asp Ala Leu Val Lys Ser
                85                  90                  95

Tyr Arg Gln Ile Thr Glu Ala Glu Arg Ala Gly Ser Thr Leu Pro
            100                 105                 110

<210> SEQ ID NO 16
<211> LENGTH: 36
<212> TYPE: PRT
<213> ORGANISM: unknown
<220> FEATURE:
<223> OTHER INFORMATION: CBD of PVP-SE1gp146 endolysin

<400> SEQUENCE: 16

Ala Ala Ile Ala Glu Ile Gln Arg Met Leu Ile Glu Gly Gly Phe Ser
1               5                   10                  15

Val Gly Lys Ser Gly Ala Asp Gly Leu Tyr Gly Pro Ala Thr Lys Ala
            20                  25                  30

Ala Leu Gln Lys
        35

<210> SEQ ID NO 17
<211> LENGTH: 56
<212> TYPE: PRT
<213> ORGANISM: unknown
<220> FEATURE:
<223> OTHER INFORMATION: CBD of endolysin 201phi2-1gp229 of Pseudomonas
      chlororaphis phage 201phi2-1

<400> SEQUENCE: 17

Lys Gly Asp Asp Val Ile Arg Leu Gln Arg Lys Leu Ile Gly Leu Gly
1               5                   10                  15

Tyr Ser Val Lys Asp Asp Gly Val Phe Gly Asp Asn Thr Glu Lys Ala
            20                  25                  30

Val Lys Ala Val Gln Leu Arg Phe Asn Leu Lys Asp Asp Gly Ile Val
        35                  40                  45

Gly Asn Asn Thr Trp Ala Val Leu
        50                  55

<210> SEQ ID NO 18
<211> LENGTH: 186
<212> TYPE: PRT
<213> ORGANISM: Artificial Sequence
<220> FEATURE:
<223> OTHER INFORMATION: peptidoglycan degrading enzyme

<400> SEQUENCE: 18

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
            20                  25                  30

Trp Ile Thr Pro Gly Val Pro Gln Ile Leu Tyr Glu Arg His Ile Met
        35                  40                  45

Ala Arg Leu Leu Lys Ala Lys Gly Val Pro Ile Ala Gly Leu Pro Ser
    50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
            100                 105                 110

Leu Cys Gly Tyr Ala Thr Val Gln Ala Phe Val Asn Ala Met Tyr Lys
        115                 120                 125

Ser Glu Asp Glu Gln Leu Asn Ala Phe Val Gly Phe Ile Lys Ser Asn
    130                 135                 140

Leu Gln Leu Asn Asp Ala Leu Lys Ser Lys Asp Trp Ala Thr Val Ala
145                 150                 155                 160

Arg Leu Tyr Asn Gly Ala Asp Tyr Lys Ile Asn Ser Tyr Asp Gln Lys
                165                 170                 175

Leu Ala Val Ala Tyr Glu Ser Asn Lys Arg
            180                 185

<210> SEQ ID NO 19
<211> LENGTH: 184
<212> TYPE: PRT
<213> ORGANISM: unknown
<220> FEATURE:
<223> OTHER INFORMATION: endolysin of Acinetobacter phage vB_AbaP_CEB1,
      w/o N.terminal methionine

<400> SEQUENCE: 19

Ile Leu Thr Lys Asp Gly Phe Gly Ile Ile Arg Asn Glu Leu Phe Gly
1               5                   10                  15

Gly Lys Leu Asp Gln Thr Gln Val Asp Ala Ile Asn Phe Ile Val Glu
            20                  25                  30

Lys Ala Thr Glu Ser Gly Leu Ser Tyr Pro Glu Ala Ala Tyr Leu Leu
        35                  40                  45

Ala Thr Ile Tyr His Glu Thr Gly Leu Pro Ser Gly Tyr Arg Thr Met

```
                    50                  55                  60
Gln Pro Ile Lys Glu Ala Gly Ser Asp Asn Tyr Leu Arg Ser Lys Lys
 65                  70                  75                  80

Tyr Tyr Pro Tyr Ile Gly Tyr Gly Tyr Val Gln Leu Thr Trp Lys Glu
                 85                  90                  95

Asn Tyr Gly Arg Ile Gly Lys Leu Ile Gly Ile Asp Leu Ile Lys Asn
            100                 105                 110

Pro Glu Lys Ala Leu Glu Pro Leu Ile Ala Ile Gln Ile Ala Ile Lys
        115                 120                 125

Gly Met Leu Asn Gly Trp Phe Thr Gly Val Gly Phe Arg Arg Lys Arg
    130                 135                 140

Pro Val Ser Lys Tyr Asn Lys Gln Gln Tyr Ile Ala Ala Arg Asn Ile
145                 150                 155                 160

Ile Asn Gly Lys Asp Lys Ala Glu Leu Ile Ala Lys Tyr Ala Ile Ile
                165                 170                 175

Phe Glu Arg Ala Leu Arg Ser Leu
            180
```

<210> SEQ ID NO 20
<211> LENGTH: 185
<212> TYPE: PRT
<213> ORGANISM: unknown
<220> FEATURE:
<223> OTHER INFORMATION: endolysin of Acinetobacter phage vB_AbaP_CEB1

<400> SEQUENCE: 20

```
Met Ile Leu Thr Lys Asp Gly Phe Gly Ile Ile Arg Asn Glu Leu Phe
  1               5                  10                  15

Gly Gly Lys Leu Asp Gln Thr Gln Val Asp Ala Ile Asn Phe Ile Val
                 20                  25                  30

Glu Lys Ala Thr Glu Ser Gly Leu Ser Tyr Pro Glu Ala Ala Tyr Leu
             35                  40                  45

Leu Ala Thr Ile Tyr His Glu Thr Gly Leu Pro Ser Gly Tyr Arg Thr
         50                  55                  60

Met Gln Pro Ile Lys Glu Ala Gly Ser Asp Asn Tyr Leu Arg Ser Lys
 65                  70                  75                  80

Lys Tyr Tyr Pro Tyr Ile Gly Tyr Gly Tyr Val Gln Leu Thr Trp Lys
                 85                  90                  95

Glu Asn Tyr Gly Arg Ile Gly Lys Leu Ile Gly Ile Asp Leu Ile Lys
            100                 105                 110

Asn Pro Glu Lys Ala Leu Glu Pro Leu Ile Ala Ile Gln Ile Ala Ile
        115                 120                 125

Lys Gly Met Leu Asn Gly Trp Phe Thr Gly Val Gly Phe Arg Arg Lys
    130                 135                 140

Arg Pro Val Ser Lys Tyr Asn Lys Gln Gln Tyr Ile Ala Ala Arg Asn
145                 150                 155                 160

Ile Ile Asn Gly Lys Asp Lys Ala Glu Leu Ile Ala Lys Tyr Ala Ile
                165                 170                 175

Ile Phe Glu Arg Ala Leu Arg Ser Leu
            180                 185
```

<210> SEQ ID NO 21
<211> LENGTH: 162
<212> TYPE: PRT
<213> ORGANISM: Salmonella phage phi68

<400> SEQUENCE: 21

Met Ser Asn Arg Asn Ile Ser Asp Asn Gly Ile Lys Phe Thr Ala Ala
1               5                   10                  15

Phe Glu Gly Phe Arg Gly Thr Ala Tyr Arg Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Val Lys Ala Val Ala Val Asp Ala Val Ala His Pro Pro Leu Asn
65                  70                  75                  80

Gln Ser Gln Phe Asp Ala Met Cys Asp Leu Val Tyr Asn Ala Gly Val
                85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
            115                 120                 125

Gly Lys Ser Leu Leu Gly Leu Arg Arg Arg Ala Ala Gly Arg Val Ala
130                 135                 140

Leu Phe Asp Gly Met Leu Trp Gln Gln Ala Glu Ala Ile Gly Arg Gly
145                 150                 155                 160

Ala Lys

<210> SEQ ID NO 22
<211> LENGTH: 132
<212> TYPE: PRT
<213> ORGANISM: Salmonella phage phi68

<400> SEQUENCE: 22

Met Ser Asn Arg Asn Ile Ser Asp Asn Gly Ile Lys Phe Thr Ala Ala
1               5                   10                  15

Phe Glu Gly Phe Arg Gly Thr Ala Tyr Arg Ala Thr Lys Asn Glu Lys
            20                  25                  30

Tyr Leu Thr Ile Gly Tyr Gly His Tyr Gly Ala Asp Val Lys Glu Gly
        35                  40                  45

Gln Lys Ile Thr Glu Gly Gln Gly Leu Leu Leu His Lys Asp Met
    50                  55                  60

Val Lys Ala Val Ala Val Asp Ala Val Ala His Pro Pro Leu Asn
65                  70                  75                  80

Gln Ser Gln Phe Asp Ala Met Cys Asp Leu Val Tyr Asn Ala Gly Val
                85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
            115                 120                 125

Gly Lys Ser Leu
    130

<210> SEQ ID NO 23
<211> LENGTH: 148
<212> TYPE: PRT
<213> ORGANISM: Salmonella phage phi68

<400> SEQUENCE: 23

Met Ser Asn Arg Asn Ile Ser Asp Asn Gly Ile Lys Phe Thr Ala Ala
1               5                   10                  15

```
Phe Glu Gly Phe Arg Gly Thr Ala Tyr Arg Ala Thr Lys Asn Glu Lys
                20                  25                  30

Tyr Leu Thr Ile Gly Tyr Gly His Tyr Gly Ala Asp Val Lys Glu Gly
            35                  40                  45

Gln Lys Ile Thr Glu Gly Gln Gly Leu Leu Leu His Lys Asp Met
 50                  55                  60

Val Lys Ala Val Ala Val Asp Ala Val Ala His Pro Pro Leu Asn
 65                  70                  75                  80

Gln Ser Gln Phe Asp Ala Met Cys Asp Leu Val Tyr Asn Ala Gly Val
                85                  90                  95

Gly Val Ile Ala Ala Ser Thr Gly Thr Gly Gln Ala Leu Arg Lys Gly
            100                 105                 110

Asp Val Ala Thr Leu Arg Asn Lys Leu Thr Gln Phe His Tyr Gln Asn
            115                 120                 125

Gly Lys Ser Leu Leu Gly Leu Arg Arg Arg Ala Ala Gly Arg Val Ala
        130                 135                 140

Leu Phe Asp Gly
145

<210> SEQ ID NO 24
<211> LENGTH: 156
<212> TYPE: PRT
<213> ORGANISM: Salmonella phage phi68

<400> SEQUENCE: 24

Ser Asp Asn Gly Ile Lys Phe Thr Ala Ala Phe Glu Gly Phe Arg Gly
1               5                   10                  15

Thr Ala Tyr Arg Ala Thr Lys Asn Glu Lys Tyr Leu Thr Ile Gly Tyr
                20                  25                  30

Gly His Tyr Gly Ala Asp Val Lys Glu Gly Gln Lys Ile Thr Glu Gly
            35                  40                  45

Gln Gly Leu Leu Leu His Lys Asp Met Val Lys Ala Val Ala Ala
 50                  55                  60

Val Asp Ala Val Ala His Pro Pro Leu Asn Gln Ser Gln Phe Asp Ala
 65                  70                  75                  80

Met Cys Asp Leu Val Tyr Asn Ala Gly Val Gly Val Ile Ala Ala Ser
                85                  90                  95

Thr Gly Thr Gly Gln Ala Leu Arg Lys Gly Asp Val Ala Thr Leu Arg
            100                 105                 110

Asn Lys Leu Thr Gln Phe His Tyr Gln Asn Gly Lys Ser Leu Leu Gly
            115                 120                 125

Leu Arg Arg Arg Ala Ala Gly Arg Val Ala Leu Phe Asp Gly Met Leu
        130                 135                 140

Trp Gln Gln Ala Glu Ala Ile Gly Arg Gly Ala Lys
145                 150                 155

<210> SEQ ID NO 25
<211> LENGTH: 161
<212> TYPE: PRT
<213> ORGANISM: Salmonella phage phi68

<400> SEQUENCE: 25

Ser Asn Arg Asn Ile Ser Asp Asn Gly Ile Lys Phe Thr Ala Ala Phe
1               5                   10                  15

Glu Gly Phe Arg Gly Thr Ala Tyr Arg Ala Thr Lys Asn Glu Lys Tyr
                20                  25                  30
```

```
Leu Thr Ile Gly Tyr Gly His Tyr Gly Ala Asp Val Lys Glu Gly Gln
        35                  40                  45

Lys Ile Thr Glu Gly Gln Gly Leu Leu Leu His Lys Asp Met Val
 50                  55                  60

Lys Ala Val Ala Ala Val Asp Ala Val Ala His Pro Pro Leu Asn Gln
 65                  70                  75                  80

Ser Gln Phe Asp Ala Met Cys Asp Leu Val Tyr Asn Ala Gly Val Gly
                85                  90                  95

Val Ile Ala Ala Ser Thr Gly Thr Gly Gln Ala Leu Arg Lys Gly Asp
                100                 105                 110

Val Ala Thr Leu Arg Asn Lys Leu Thr Gln Phe His Tyr Gln Asn Gly
                115                 120                 125

Lys Ser Leu Leu Gly Leu Arg Arg Arg Ala Ala Gly Arg Val Ala Leu
        130                 135                 140

Phe Asp Gly Met Leu Trp Gln Gln Ala Glu Ala Ile Gly Arg Gly Ala
145                 150                 155                 160

Lys
```

<210> SEQ ID NO 26
<211> LENGTH: 161
<212> TYPE: PRT
<213> ORGANISM: Artificial sequence
<220> FEATURE:
<223> OTHER INFORMATION: Lys68 (P78S) w/o Met

<400> SEQUENCE: 26

```
Ser Asn Arg Asn Ile Ser Asp Asn Gly Ile Lys Phe Thr Ala Ala Phe
 1               5                  10                  15

Glu Gly Phe Arg Gly Thr Ala Tyr Arg Ala Thr Lys Asn Glu Lys Tyr
                20                  25                  30

Leu Thr Ile Gly Tyr Gly His Tyr Gly Ala Asp Val Lys Glu Gly Gln
        35                  40                  45

Lys Ile Thr Glu Gly Gln Gly Leu Leu Leu His Lys Asp Met Val
 50                  55                  60

Lys Ala Val Ala Ala Val Asp Ala Val Ala His Pro Ser Leu Asn Gln
 65                  70                  75                  80

Ser Gln Phe Asp Ala Met Cys Asp Leu Val Tyr Asn Ala Gly Val Gly
                85                  90                  95

Val Ile Ala Ala Ser Thr Gly Thr Gly Gln Ala Leu Arg Lys Gly Asp
                100                 105                 110

Val Ala Thr Leu Arg Asn Lys Leu Thr Gln Phe His Tyr Gln Asn Gly
                115                 120                 125

Lys Ser Leu Leu Gly Leu Arg Arg Arg Ala Ala Gly Arg Val Ala Leu
        130                 135                 140

Phe Asp Gly Met Leu Trp Gln Gln Ala Glu Ala Ile Gly Arg Gly Ala
145                 150                 155                 160

Lys
```

<210> SEQ ID NO 27
<211> LENGTH: 136
<212> TYPE: PRT
<213> ORGANISM: Unknown
<220> FEATURE:
<223> OTHER INFORMATION: S394 endolysin without N-terminal methionine

<400> SEQUENCE: 27

```
Ser Phe Lys Phe Gly Lys Asn Ser Glu Lys Gln Leu Ala Thr Val Lys
```

```
            1               5                  10                 15
        Pro Glu Leu Gln Lys Val Ala Arg Ala Leu Glu Leu Ser Pro Tyr
                    20                  25                  30

Asp Phe Thr Ile Val Gln Gly Ile Arg Thr Val Ala Gln Ser Ala Gln
                    35                  40                  45

Asn Ile Ala Asn Gly Thr Ser Phe Leu Lys Asp Pro Ser Lys Ser Lys
                    50                  55                  60

His Val Thr Gly Asp Ala Ile Asp Phe Ala Pro Tyr Ile Asn Gly Lys
         65                  70                  75                  80

Ile Asp Trp Lys Asp Leu Glu Ala Phe Trp Ala Val Lys Lys Ala Phe
                        85                  90                  95

Glu Gln Ala Gly Lys Glu Leu Gly Ile Lys Leu Arg Phe Gly Ala Asp
                        100                 105                 110

Trp Asn Ser Ser Gly Asp Tyr His Asp Glu Ile Asp Arg Gly Thr Tyr
                        115                 120                 125

Asp Gly Gly His Val Glu Leu Val
                    130                 135
```

<210> SEQ ID NO 28
<211> LENGTH: 137
<212> TYPE: PRT
<213> ORGANISM: Bacteriophage S-394

<400> SEQUENCE: 28

```
        Met Ser Phe Lys Phe Gly Lys Asn Ser Glu Lys Gln Leu Ala Thr Val
         1               5                  10                  15

Lys Pro Glu Leu Gln Lys Val Ala Arg Ala Leu Glu Leu Ser Pro
                        20                  25                  30

Tyr Asp Phe Thr Ile Val Gln Gly Ile Arg Thr Val Ala Gln Ser Ala
                        35                  40                  45

Gln Asn Ile Ala Asn Gly Thr Ser Phe Leu Lys Asp Pro Ser Lys Ser
                    50                  55                  60

Lys His Val Thr Gly Asp Ala Ile Asp Phe Ala Pro Tyr Ile Asn Gly
         65                  70                  75                  80

Lys Ile Asp Trp Lys Asp Leu Glu Ala Phe Trp Ala Val Lys Lys Ala
                        85                  90                  95

Phe Glu Gln Ala Gly Lys Glu Leu Gly Ile Lys Leu Arg Phe Gly Ala
                        100                 105                 110

Asp Trp Asn Ser Ser Gly Asp Tyr His Asp Glu Ile Asp Arg Gly Thr
                        115                 120                 125

Tyr Asp Gly Gly His Val Glu Leu Val
                    130                 135
```

<210> SEQ ID NO 29
<211> LENGTH: 275
<212> TYPE: PRT
<213> ORGANISM: artificial sequence
<220> FEATURE:
<223> OTHER INFORMATION: Fusion of CBD of EL188 endolysin with ABgp46
      endolysin

<400> SEQUENCE: 29

```
        Met Asn Phe Arg Thr Lys Asn Gly Tyr Arg Asp Leu Gln Ala Leu Val
         1               5                  10                  15

Lys Glu Leu Gly Leu Tyr Thr Gly Gln Ile Asp Gly Val Trp Gly Lys
                        20                  25                  30

Gly Thr Ser Ser Ser Thr Glu Thr Leu Leu Arg Gly Tyr Ala Glu Val
```

```
        35                  40                  45
Val Gly Lys Asn Thr Gly Gly Ile Gly Leu Pro Thr Thr Ser Asp Ala
 50                  55                  60
Ser Gly Tyr Asn Val Ile Thr Ala Leu Gln Arg Asn Leu Ala Phe Leu
65                  70                  75                  80
Gly Leu Tyr Ser Leu Thr Val Asp Gly Ile Trp Asn Gly Thr Leu
                85                  90                  95
Ser Gly Leu Asp Lys Ala Phe Glu Val Tyr Lys Glu Arg Tyr Arg Thr
               100                 105                 110
Pro Thr Ser Asn Arg Asn Ile Ser Asp Asn Gly Ile Lys Phe Thr Ala
               115                 120                 125
Ala Phe Glu Gly Phe Arg Gly Thr Ala Tyr Arg Ala Thr Lys Asn Glu
       130                 135                 140
Lys Tyr Leu Thr Ile Gly Tyr Gly His Tyr Gly Ala Asp Val Lys Glu
145                 150                 155                 160
Gly Gln Lys Ile Thr Glu Gly Gln Gly Leu Leu Leu Leu His Lys Asp
                165                 170                 175
Met Val Lys Ala Val Ala Ala Val Asp Ala Val Ala His Pro Pro Leu
               180                 185                 190
Asn Gln Ser Gln Phe Asp Ala Met Ser Asp Leu Val Tyr Asn Ala Gly
           195                 200                 205
Val Gly Val Ile Ala Ala Ser Thr Gly Thr Gly Gln Ala Leu Arg Lys
       210                 215                 220
Gly Asp Val Ala Thr Leu Arg Asn Lys Leu Thr Gln Phe His Tyr Gln
225                 230                 235                 240
Asn Gly Lys Ser Leu Leu Gly Leu Arg Arg Arg Ala Ala Gly Arg Val
                245                 250                 255
Ala Leu Phe Asp Gly Met Leu Trp Gln Gln Ala Glu Ala Ile Gly Arg
               260                 265                 270
Gly Ala Lys
       275

<210> SEQ ID NO 30
<211> LENGTH: 230
<212> TYPE: PRT
<213> ORGANISM: artificial sequence
<220> FEATURE:
<223> OTHER INFORMATION: Fusion of CBD of KZ144 endolysin  (three
      cysteines replaced by serine) with LYS68 endolysin

<400> SEQUENCE: 30

Met Lys Val Leu Arg Lys Gly Asp Arg Gly Asp Glu Val Ser Gln Leu
1               5                  10                  15
Gln Thr Leu Leu Asn Leu Ser Gly Tyr Asp Val Gly Lys Pro Asp Gly
            20                  25                  30
Ile Phe Gly Asn Asn Thr Phe Asn Gln Val Val Lys Phe Gln Lys Asp
        35                  40                  45
Asn Ser Leu Asp Ser Asp Gly Ile Val Gly Lys Thr Trp Ala Glu
 50                  55                  60
Leu Phe Ser Lys Tyr Ser Asn Arg Asn Ile Ser Asp Asn Gly Ile Lys
65                  70                  75                  80
Phe Thr Ala Ala Phe Glu Gly Phe Arg Gly Thr Ala Tyr Arg Ala Thr
                85                  90                  95
Lys Asn Glu Lys Tyr Leu Thr Ile Gly Tyr Gly His Tyr Gly Ala Asp
               100                 105                 110
```

```
Val Lys Glu Gly Gln Lys Ile Thr Glu Gly Gln Gly Leu Leu Leu
        115                 120                 125

His Lys Asp Met Val Lys Ala Val Ala Ala Val Asp Ala Val Ala His
130                 135                 140

Pro Pro Leu Asn Gln Ser Gln Phe Asp Ala Met Cys Asp Leu Val Tyr
145                 150                 155                 160

Asn Ala Gly Val Gly Val Ile Ala Ala Ser Thr Gly Thr Gly Gln Ala
                    165                 170                 175

Leu Arg Lys Gly Asp Val Ala Thr Leu Arg Asn Lys Leu Thr Gln Phe
                180                 185                 190

His Tyr Gln Asn Gly Lys Ser Leu Leu Gly Leu Arg Arg Arg Ala Ala
                195                 200                 205

Gly Arg Val Ala Leu Phe Asp Gly Met Leu Trp Gln Gln Ala Glu Ala
210                 215                 220

Ile Gly Arg Gly Ala Lys
225                 230

<210> SEQ ID NO 31
<211> LENGTH: 254
<212> TYPE: PRT
<213> ORGANISM: artificial sequence
<220> FEATURE:
<223> OTHER INFORMATION: Fusion of CBD of KZ144 endolysin  (three
      cysteines replaced by serine) with ABgp46 endolysin

<400> SEQUENCE: 31

Met Lys Val Leu Arg Lys Gly Asp Arg Gly Asp Glu Val Ser Gln Leu
1               5                   10                  15

Gln Thr Leu Leu Asn Leu Ser Gly Tyr Asp Val Gly Lys Pro Asp Gly
                20                  25                  30

Ile Phe Gly Asn Asn Thr Phe Asn Gln Val Val Lys Phe Gln Lys Asp
            35                  40                  45

Asn Ser Leu Asp Ser Asp Gly Ile Val Gly Lys Asn Thr Trp Ala Glu
50                  55                  60

Leu Phe Ser Lys Tyr Ser Ile Leu Thr Lys Asp Gly Phe Gly Ile Ile
65                  70                  75                  80

Arg Asn Glu Leu Phe Gly Gly Lys Leu Asp Gln Thr Gln Val Asp Ala
                85                  90                  95

Ile Asn Phe Ile Val Glu Lys Ala Thr Glu Ser Gly Leu Ser Tyr Pro
            100                 105                 110

Glu Ala Ala Tyr Leu Leu Ala Thr Ile Tyr His Glu Thr Gly Leu Pro
        115                 120                 125

Ser Gly Tyr Arg Thr Met Gln Pro Ile Lys Glu Ala Gly Ser Asp Asn
130                 135                 140

Tyr Leu Arg Ser Lys Lys Tyr Tyr Pro Tyr Ile Gly Tyr Gly Tyr Val
145                 150                 155                 160

Gln Leu Thr Trp Lys Glu Asn Tyr Gly Arg Ile Gly Lys Leu Ile Gly
                165                 170                 175

Ile Asp Leu Ile Lys Asn Pro Glu Lys Ala Leu Glu Pro Leu Ile Ala
            180                 185                 190

Ile Gln Ile Ala Ile Lys Gly Met Leu Asn Gly Trp Phe Thr Gly Val
        195                 200                 205

Gly Phe Arg Arg Lys Arg Pro Val Ser Lys Tyr Asn Lys Gln Gln Tyr
210                 215                 220

Ile Ala Ala Arg Asn Ile Ile Asn Gly Lys Asp Lys Ala Glu Leu Ile
225                 230                 235                 240
```

```
Ala Lys Tyr Ala Ile Ile Phe Glu Arg Ala Leu Arg Ser Leu
            245                 250

<210> SEQ ID NO 32
<211> LENGTH: 263
<212> TYPE: PRT
<213> ORGANISM: Artificial sequence
<220> FEATURE:
<223> OTHER INFORMATION: Fusion of CBD of ICP endolysin with ABgp46
      endolysin

<400> SEQUENCE: 32

Met Ile Leu Lys Arg Gly Ser Ser Gly Ala Asp Val Lys Asn Met Gln
1               5                   10                  15

Glu Tyr Leu Thr Ala Leu Gly Tyr Asp Thr Lys Gly Val Glu Gly Thr
            20                  25                  30

Phe Glu Gly Gly Thr Glu Ser Ala Val Lys Ala Phe Gln Lys Asp Met
        35                  40                  45

Ser Phe Thr Val Val Asp Gly Ile Ile Gly Asn Gln Thr Ala Lys His
    50                  55                  60

Leu Val Asp Met Tyr Tyr Gly Lys Val Pro Phe Gly Tyr Val Ile
65                  70                  75                  80

Leu Thr Lys Asp Gly Phe Gly Ile Ile Arg Asn Glu Leu Phe Gly Gly
                85                  90                  95

Lys Leu Asp Gln Thr Gln Val Asp Ala Ile Asn Phe Ile Val Glu Lys
            100                 105                 110

Ala Thr Glu Ser Gly Leu Ser Tyr Pro Glu Ala Ala Tyr Leu Leu Ala
        115                 120                 125

Thr Ile Tyr His Glu Thr Gly Leu Pro Ser Gly Tyr Arg Thr Met Gln
    130                 135                 140

Pro Ile Lys Glu Ala Gly Ser Asp Asn Tyr Leu Arg Ser Lys Lys Tyr
145                 150                 155                 160

Tyr Pro Tyr Ile Gly Tyr Gly Tyr Val Gln Leu Thr Trp Lys Glu Asn
                165                 170                 175

Tyr Gly Arg Ile Gly Lys Leu Ile Gly Ile Asp Leu Ile Lys Asn Pro
            180                 185                 190

Glu Lys Ala Leu Glu Pro Leu Ile Ala Ile Gln Ile Ala Ile Lys Gly
        195                 200                 205

Met Leu Asn Gly Trp Phe Thr Gly Val Gly Phe Arg Arg Lys Arg Pro
    210                 215                 220

Val Ser Lys Tyr Asn Lys Gln Gln Tyr Ile Ala Ala Arg Asn Ile Ile
225                 230                 235                 240

Asn Gly Lys Asp Lys Ala Glu Leu Ile Ala Lys Tyr Ala Ile Ile Phe
                245                 250                 255

Glu Arg Ala Leu Arg Ser Leu
            260

<210> SEQ ID NO 33
<211> LENGTH: 215
<212> TYPE: PRT
<213> ORGANISM: artificial sequence
<220> FEATURE:
<223> OTHER INFORMATION: Fusion of CBD of ICP endolysin with LYS394
      endolysin

<400> SEQUENCE: 33

Met Ile Leu Lys Arg Gly Ser Ser Gly Ala Asp Val Lys Asn Met Gln
1               5                   10                  15
```

Glu Tyr Leu Thr Ala Leu Gly Tyr Asp Thr Lys Gly Val Glu Gly Thr
                20                  25                  30

Phe Glu Gly Gly Thr Glu Ser Ala Val Lys Ala Phe Gln Lys Asp Met
            35                  40                  45

Ser Phe Thr Val Val Asp Gly Ile Ile Gly Asn Gln Thr Ala Lys His
 50                  55                  60

Leu Val Asp Met Tyr Tyr Gly Lys Val Pro Phe Gly Tyr Val Ser
 65                  70                  75                  80

Phe Lys Phe Gly Lys Asn Ser Glu Lys Gln Leu Ala Thr Val Lys Pro
                85                  90                  95

Glu Leu Gln Lys Val Ala Arg Arg Ala Leu Glu Leu Ser Pro Tyr Asp
            100                 105                 110

Phe Thr Ile Val Gln Gly Ile Arg Thr Val Ala Gln Ser Ala Gln Asn
        115                 120                 125

Ile Ala Asn Gly Thr Ser Phe Leu Lys Asp Pro Ser Lys Ser Lys His
130                 135                 140

Val Thr Gly Asp Ala Ile Asp Phe Ala Pro Tyr Ile Asn Gly Lys Ile
145                 150                 155                 160

Asp Trp Lys Asp Leu Glu Ala Phe Trp Ala Val Lys Lys Ala Phe Glu
                165                 170                 175

Gln Ala Gly Lys Glu Leu Gly Ile Lys Leu Arg Phe Gly Ala Asp Trp
            180                 185                 190

Asn Ser Ser Gly Asp Tyr His Asp Glu Ile Asp Arg Gly Thr Tyr Asp
        195                 200                 205

Gly Gly His Val Glu Leu Val
    210                 215

<210> SEQ ID NO 34
<211> LENGTH: 230
<212> TYPE: PRT
<213> ORGANISM: artificial sequence
<220> FEATURE:
<223> OTHER INFORMATION: Fusion of CBD of KZ144 endolysin (three
      cysteines replaced by serine) with LYS68 endolysin

<400> SEQUENCE: 34

Met Lys Val Leu Arg Lys Gly Asp Arg Gly Asp Glu Val Ser Gln Leu
1               5                   10                  15

Gln Thr Leu Leu Asn Leu Ser Gly Tyr Asp Val Gly Lys Pro Asp Gly
                20                  25                  30

Ile Phe Gly Asn Asn Thr Phe Asn Gln Val Val Lys Phe Gln Lys Asp
            35                  40                  45

Asn Ser Leu Asp Ser Asp Gly Ile Val Gly Met Asn Thr Trp Ala Glu
 50                  55                  60

Leu Phe Ser Lys Tyr Ser Asn Arg Asn Ile Ser Asp Asn Gly Ile Lys
 65                  70                  75                  80

Phe Thr Ala Ala Phe Glu Gly Phe Arg Gly Thr Ala Tyr Arg Ala Thr
                85                  90                  95

Lys Asn Glu Lys Tyr Leu Thr Ile Gly Tyr Gly His Tyr Gly Ala Asp
            100                 105                 110

Val Lys Glu Gly Gln Lys Ile Thr Glu Gly Gln Gly Leu Leu Leu
        115                 120                 125

His Lys Asp Met Val Lys Ala Val Ala Ala Val Asp Ala Val Ala His
130                 135                 140

Pro Ser Leu Asn Gln Ser Gln Phe Asp Ala Met Cys Asp Leu Val Tyr

```
            145                 150                 155                 160
Asn Ala Gly Val Gly Val Ile Ala Ala Ser Thr Gly Thr Gly Gln Ala
                165                 170                 175
Leu Arg Lys Gly Asp Val Ala Thr Leu Arg Asn Lys Leu Thr Gln Phe
            180                 185                 190
His Tyr Gln Asn Gly Lys Ser Leu Leu Gly Leu Arg Arg Ala Ala
        195                 200                 205
Gly Arg Val Ala Leu Phe Asp Gly Met Leu Trp Gln Gln Ala Glu Ala
    210                 215                 220
Ile Gly Arg Gly Ala Lys
225                 230

<210> SEQ ID NO 35
<211> LENGTH: 274
<212> TYPE: PRT
<213> ORGANISM: artificial sequence
<220> FEATURE:
<223> OTHER INFORMATION: Fusion of CBD of EL188 endolysin with ABgp46
      endolysin w/o starting methionine

<400> SEQUENCE: 35

Asn Phe Arg Thr Lys Asn Gly Tyr Arg Asp Leu Gln Ala Leu Val Lys
1               5                  10                  15
Glu Leu Gly Leu Tyr Thr Gly Gln Ile Asp Gly Val Trp Gly Lys Gly
            20                  25                  30
Thr Ser Ser Thr Glu Thr Leu Leu Arg Gly Tyr Ala Glu Val Val
        35                  40                  45
Gly Lys Asn Thr Gly Gly Ile Gly Leu Pro Thr Thr Ser Asp Ala Ser
    50                  55                  60
Gly Tyr Asn Val Ile Thr Ala Leu Gln Arg Asn Leu Ala Phe Leu Gly
65                  70                  75                  80
Leu Tyr Ser Leu Thr Val Asp Gly Ile Trp Gly Asn Gly Thr Leu Ser
                85                  90                  95
Gly Leu Asp Lys Ala Phe Glu Val Tyr Lys Glu Arg Tyr Arg Thr Pro
            100                 105                 110
Thr Ser Asn Arg Asn Ile Ser Asp Asn Gly Ile Lys Phe Thr Ala Ala
        115                 120                 125
Phe Glu Gly Phe Arg Gly Thr Ala Tyr Arg Ala Thr Lys Asn Glu Lys
    130                 135                 140
Tyr Leu Thr Ile Gly Tyr Gly His Tyr Gly Ala Asp Val Lys Glu Gly
145                 150                 155                 160
Gln Lys Ile Thr Glu Gly Gln Gly Leu Leu Leu His Lys Asp Met
                165                 170                 175
Val Lys Ala Val Ala Val Asp Ala Val Ala His Pro Pro Leu Asn
            180                 185                 190
Gln Ser Gln Phe Asp Ala Met Ser Asp Leu Val Tyr Asn Ala Gly Val
        195                 200                 205
Gly Val Ile Ala Ala Ser Thr Gly Thr Gly Gln Ala Leu Arg Lys Gly
    210                 215                 220
Asp Val Ala Thr Leu Arg Asn Lys Leu Thr Gln Phe His Tyr Gln Asn
225                 230                 235                 240
Gly Lys Ser Leu Leu Gly Leu Arg Arg Ala Ala Gly Arg Val Ala
                245                 250                 255
Leu Phe Asp Gly Met Leu Trp Gln Gln Ala Glu Ala Ile Gly Arg Gly
            260                 265                 270
```

Ala Lys

<210> SEQ ID NO 36
<211> LENGTH: 229
<212> TYPE: PRT
<213> ORGANISM: artificial sequence
<220> FEATURE:
<223> OTHER INFORMATION: Fusion of CBD of KZ144 endolysin (three
      cysteines replaced by serine) with LYS68 endolysin w/o starting
      methionine

<400> SEQUENCE: 36

```
Lys Val Leu Arg Lys Gly Asp Arg Gly Asp Glu Val Ser Gln Leu Gln
1               5                   10                  15

Thr Leu Leu Asn Leu Ser Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
    50                  55                  60

Phe Ser Lys Tyr Ser Asn Arg Asn Ile Ser Asp Asn Gly Ile Lys Phe
65                  70                  75                  80

Thr Ala Ala Phe Glu Gly Phe Arg Gly Thr Ala Tyr Arg Ala Thr Lys
                85                  90                  95

Asn Glu Lys Tyr Leu Thr Ile Gly Tyr Gly His Tyr Gly Ala Asp Val
            100                 105                 110

Lys Glu Gly Gln Lys Ile Thr Glu Gly Gln Gly Leu Leu Leu Leu His
        115                 120                 125

Lys Asp Met Val Lys Ala Val Ala Val Asp Ala Val Ala His Pro
    130                 135                 140

Pro Leu Asn Gln Ser Gln Phe Asp Ala Met Cys Asp Leu Val Tyr Asn
145                 150                 155                 160

Ala Gly Val Gly Val Ile Ala Ala Ser Thr Gly Thr Gly Gln Ala Leu
                165                 170                 175

Arg Lys Gly Asp Val Ala Thr Leu Arg Asn Lys Leu Thr Gln Phe His
            180                 185                 190

Tyr Gln Asn Gly Lys Ser Leu Leu Gly Leu Arg Arg Arg Ala Ala Gly
        195                 200                 205

Arg Val Ala Leu Phe Asp Gly Met Leu Trp Gln Gln Ala Glu Ala Ile
    210                 215                 220

Gly Arg Gly Ala Lys
225
```

<210> SEQ ID NO 37
<211> LENGTH: 253
<212> TYPE: PRT
<213> ORGANISM: artificial sequence
<220> FEATURE:
<223> OTHER INFORMATION: Fusion of CBD of KZ144 endolysin (three
      cysteines replaced by serine) with ABgp46 endolysin w/o starting
      methionine

<400> SEQUENCE: 37

```
Lys Val Leu Arg Lys Gly Asp Arg Gly Asp Glu Val Ser Gln Leu Gln
1               5                   10                  15

Thr Leu Leu Asn Leu Ser Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45
```

```
Ser Leu Asp Ser Asp Gly Ile Val Gly Lys Asn Thr Trp Ala Glu Leu
 50                  55                  60

Phe Ser Lys Tyr Ser Ile Leu Thr Lys Asp Gly Phe Gly Ile Ile Arg
 65                  70                  75                  80

Asn Glu Leu Phe Gly Gly Lys Leu Asp Gln Thr Gln Val Asp Ala Ile
                 85                  90                  95

Asn Phe Ile Val Glu Lys Ala Thr Glu Ser Gly Leu Ser Tyr Pro Glu
            100                 105                 110

Ala Ala Tyr Leu Leu Ala Thr Ile Tyr His Glu Thr Gly Leu Pro Ser
        115                 120                 125

Gly Tyr Arg Thr Met Gln Pro Ile Lys Glu Ala Gly Ser Asp Asn Tyr
    130                 135                 140

Leu Arg Ser Lys Lys Tyr Tyr Pro Tyr Ile Gly Tyr Gly Tyr Val Gln
145                 150                 155                 160

Leu Thr Trp Lys Glu Asn Tyr Gly Arg Ile Gly Lys Leu Ile Gly Ile
                165                 170                 175

Asp Leu Ile Lys Asn Pro Glu Lys Ala Leu Glu Pro Leu Ile Ala Ile
            180                 185                 190

Gln Ile Ala Ile Lys Gly Met Leu Asn Gly Trp Phe Thr Gly Val Gly
        195                 200                 205

Phe Arg Arg Lys Arg Pro Val Ser Lys Tyr Asn Lys Gln Gln Tyr Ile
    210                 215                 220

Ala Ala Arg Asn Ile Ile Asn Gly Lys Asp Lys Ala Glu Leu Ile Ala
225                 230                 235                 240

Lys Tyr Ala Ile Ile Phe Glu Arg Ala Leu Arg Ser Leu
                245                 250

<210> SEQ ID NO 38
<211> LENGTH: 262
<212> TYPE: PRT
<213> ORGANISM: Artificial sequence
<220> FEATURE:
<223> OTHER INFORMATION: Fusion of CBD of ICP endolysin with ABgp46
      endolysin w/o starting methionine

<400> SEQUENCE: 38

Ile Leu Lys Arg Gly Ser Ser Gly Ala Asp Val Lys Asn Met Gln Glu
 1               5                  10                  15

Tyr Leu Thr Ala Leu Gly Tyr Asp Thr Lys Gly Val Glu Gly Thr Phe
                 20                  25                  30

Glu Gly Gly Thr Glu Ser Ala Val Lys Ala Phe Gln Lys Asp Met Ser
            35                  40                  45

Phe Thr Val Val Asp Gly Ile Ile Gly Asn Gln Thr Ala Lys His Leu
 50                  55                  60

Val Asp Met Tyr Tyr Gly Lys Val Val Pro Phe Gly Tyr Val Ile Leu
 65                  70                  75                  80

Thr Lys Asp Gly Phe Gly Ile Ile Arg Asn Glu Leu Phe Gly Gly Lys
                 85                  90                  95

Leu Asp Gln Thr Gln Val Asp Ala Ile Asn Phe Ile Val Glu Lys Ala
            100                 105                 110

Thr Glu Ser Gly Leu Ser Tyr Pro Glu Ala Ala Tyr Leu Leu Ala Thr
        115                 120                 125

Ile Tyr His Glu Thr Gly Leu Pro Ser Gly Tyr Arg Thr Met Gln Pro
    130                 135                 140

Ile Lys Glu Ala Gly Ser Asp Asn Tyr Leu Arg Ser Lys Lys Tyr Tyr
```

Pro Tyr Ile Gly Tyr Gly Tyr Val Gln Leu Thr Trp Lys Glu Asn Tyr
145                 150                 155                 160

Gly Arg Ile Gly Lys Leu Ile Gly Ile Asp Leu Ile Lys Asn Pro Glu
            165                 170                 175

Lys Ala Leu Glu Pro Leu Ile Ala Ile Gln Ile Ala Ile Lys Gly Met
            180                 185                 190

Leu Asn Gly Trp Phe Thr Gly Val Gly Phe Arg Arg Lys Arg Pro Val
            195                 200                 205

Ser Lys Tyr Asn Lys Gln Gln Tyr Ile Ala Ala Arg Asn Ile Ile Asn
210                 215                 220

Gly Lys Asp Lys Ala Glu Leu Ile Ala Lys Tyr Ala Ile Ile Phe Glu
225                 230                 235                 240

Arg Ala Leu Arg Ser Leu
            245                 250                 255

260

<210> SEQ ID NO 39
<211> LENGTH: 214
<212> TYPE: PRT
<213> ORGANISM: artificial sequence
<220> FEATURE:
<223> OTHER INFORMATION: Fusion of CBD of ICP endolysin with LYS394
      endolysin w/o starting methionine

<400> SEQUENCE: 39

Ile Leu Lys Arg Gly Ser Ser Gly Ala Asp Val Lys Asn Met Gln Glu
1               5                   10                  15

Tyr Leu Thr Ala Leu Gly Tyr Asp Thr Lys Gly Val Glu Gly Thr Phe
            20                  25                  30

Glu Gly Gly Thr Glu Ser Ala Val Lys Ala Phe Gln Lys Asp Met Ser
        35                  40                  45

Phe Thr Val Val Asp Gly Ile Ile Gly Asn Gln Thr Ala Lys His Leu
    50                  55                  60

Val Asp Met Tyr Tyr Gly Lys Val Val Pro Phe Gly Tyr Val Ser Phe
65                  70                  75                  80

Lys Phe Gly Lys Asn Ser Glu Lys Gln Leu Ala Thr Val Lys Pro Glu
                85                  90                  95

Leu Gln Lys Val Ala Arg Arg Ala Leu Glu Leu Ser Pro Tyr Asp Phe
            100                 105                 110

Thr Ile Val Gln Gly Ile Arg Thr Val Ala Gln Ser Ala Gln Asn Ile
        115                 120                 125

Ala Asn Gly Thr Ser Phe Leu Lys Asp Pro Ser Lys Ser Lys His Val
    130                 135                 140

Thr Gly Asp Ala Ile Asp Phe Ala Pro Tyr Ile Asn Gly Lys Ile Asp
145                 150                 155                 160

Trp Lys Asp Leu Glu Ala Phe Trp Ala Val Lys Lys Ala Phe Glu Gln
                165                 170                 175

Ala Gly Lys Glu Leu Gly Ile Lys Leu Arg Phe Gly Ala Asp Trp Asn
            180                 185                 190

Ser Ser Gly Asp Tyr His Asp Glu Ile Asp Arg Gly Thr Tyr Asp Gly
        195                 200                 205

Gly His Val Glu Leu Val
    210

<210> SEQ ID NO 40
<211> LENGTH: 229

```
<212> TYPE: PRT
<213> ORGANISM: artificial sequence
<220> FEATURE:
<223> OTHER INFORMATION: Fusion of CBD of KZ144 endolysin (three
      cysteines replaced by serine) with LYS68 endolysin w/o starting
      methionine

<400> SEQUENCE: 40
```

| | | | | | | | | | | | | | | | |
|---|---|---|---|---|---|---|---|---|---|---|---|---|---|---|---|
| Lys | Val | Leu | Arg | Lys | Gly | Asp | Arg | Gly | Asp | Glu | Val | Ser | Gln | Leu | Gln |
| 1 | | | | 5 | | | | | 10 | | | | | 15 | |
| Thr | Leu | Leu | Asn | Leu | Ser | Gly | Tyr | Asp | Val | Gly | Lys | Pro | Asp | Gly | Ile |
| | | | 20 | | | | | 25 | | | | | 30 | | |
| Phe | Gly | Asn | Asn | Thr | Phe | Asn | Gln | Val | Val | Lys | Phe | Gln | Lys | Asp | Asn |
| | | | | 35 | | | | | 40 | | | | 45 | | |
| Ser | Leu | Asp | Ser | Asp | Gly | Ile | Val | Gly | Met | Asn | Thr | Trp | Ala | Glu | Leu |
| 50 | | | | | 55 | | | | | 60 | | | | | |
| Phe | Ser | Lys | Tyr | Ser | Asn | Arg | Asn | Ile | Ser | Asp | Asn | Gly | Ile | Lys | Phe |
| 65 | | | | | 70 | | | | | 75 | | | | | 80 |
| Thr | Ala | Ala | Phe | Glu | Gly | Phe | Arg | Gly | Thr | Ala | Tyr | Arg | Ala | Thr | Lys |
| | | | | 85 | | | | | 90 | | | | | 95 | |
| Asn | Glu | Lys | Tyr | Leu | Thr | Ile | Gly | Tyr | Gly | His | Tyr | Gly | Ala | Asp | Val |
| | | | 100 | | | | | 105 | | | | | 110 | | |
| Lys | Glu | Gly | Gln | Lys | Ile | Thr | Glu | Gly | Gln | Gly | Leu | Leu | Leu | Leu | His |
| | | | 115 | | | | | 120 | | | | | 125 | | |
| Lys | Asp | Met | Val | Lys | Ala | Val | Ala | Ala | Val | Asp | Val | Ala | His | Pro | |
| | | 130 | | | | | 135 | | | | | 140 | | | |
| Ser | Leu | Asn | Gln | Ser | Gln | Phe | Asp | Ala | Met | Cys | Asp | Leu | Val | Tyr | Asn |
| 145 | | | | | 150 | | | | | 155 | | | | | 160 |
| Ala | Gly | Val | Gly | Val | Ile | Ala | Ala | Ser | Thr | Gly | Thr | Gly | Gln | Ala | Leu |
| | | | | 165 | | | | | 170 | | | | | 175 | |
| Arg | Lys | Gly | Asp | Val | Ala | Thr | Leu | Arg | Asn | Lys | Leu | Thr | Gln | Phe | His |
| | | | 180 | | | | | 185 | | | | | 190 | | |
| Tyr | Gln | Asn | Gly | Lys | Ser | Leu | Leu | Gly | Leu | Arg | Arg | Arg | Ala | Ala | Gly |
| | | | 195 | | | | | 200 | | | | | 205 | | |
| Arg | Val | Ala | Leu | Phe | Asp | Gly | Met | Leu | Trp | Gln | Gln | Ala | Glu | Ala | Ile |
| | 210 | | | | | 215 | | | | | 220 | | | | |
| Gly | Arg | Gly | Ala | Lys | | | | | | | | | | | |
| 225 | | | | | | | | | | | | | | | |

```
<210> SEQ ID NO 41
<211> LENGTH: 6
<212> TYPE: PRT
<213> ORGANISM: artificial
<220> FEATURE:
<223> OTHER INFORMATION: synthetic sequence

<400> SEQUENCE: 41

Lys Arg Lys Lys Arg Lys
1               5

<210> SEQ ID NO 42
<211> LENGTH: 5
<212> TYPE: PRT
<213> ORGANISM: artificial
<220> FEATURE:
<223> OTHER INFORMATION: synethtic sequence
<220> FEATURE:
<221> NAME/KEY: misc_feature
<222> LOCATION: (3)..(3)
<223> OTHER INFORMATION: Xaa can be any naturally occurring amino acid
```

```
<400> SEQUENCE: 42

Lys Arg Xaa Lys Arg
1               5

<210> SEQ ID NO 43
<211> LENGTH: 5
<212> TYPE: PRT
<213> ORGANISM: artificial
<220> FEATURE:
<223> OTHER INFORMATION: synthetic sequence

<400> SEQUENCE: 43

Lys Arg Ser Lys Arg
1               5

<210> SEQ ID NO 44
<211> LENGTH: 5
<212> TYPE: PRT
<213> ORGANISM: artificial
<220> FEATURE:
<223> OTHER INFORMATION: synthetic sequence

<400> SEQUENCE: 44

Lys Arg Gly Ser Gly
1               5

<210> SEQ ID NO 45
<211> LENGTH: 9
<212> TYPE: PRT
<213> ORGANISM: artificial
<220> FEATURE:
<223> OTHER INFORMATION: synthetic sequence

<400> SEQUENCE: 45

Lys Arg Lys Lys Arg Lys Lys Arg Lys
1               5

<210> SEQ ID NO 46
<211> LENGTH: 9
<212> TYPE: PRT
<213> ORGANISM: artificial
<220> FEATURE:
<223> OTHER INFORMATION: synthetic sequence

<400> SEQUENCE: 46

Arg Arg Arg Arg Arg Arg Arg Arg Arg
1               5

<210> SEQ ID NO 47
<211> LENGTH: 8
<212> TYPE: PRT
<213> ORGANISM: artificial
<220> FEATURE:
<223> OTHER INFORMATION: synthetic sequence

<400> SEQUENCE: 47

Lys Lys Lys Lys Lys Lys Lys Lys
1               5

<210> SEQ ID NO 48
<211> LENGTH: 10
<212> TYPE: PRT
<213> ORGANISM: artificial
<220> FEATURE:
<223> OTHER INFORMATION: synthetic sequence

<400> SEQUENCE: 48
```

```
Lys Arg Lys Lys Arg Lys Lys Arg Lys Lys
1               5                   10

<210> SEQ ID NO 49
<211> LENGTH: 12
<212> TYPE: PRT
<213> ORGANISM: artificial
<220> FEATURE:
<223> OTHER INFORMATION: synthetic sequence

<400> SEQUENCE: 49

Lys Arg Lys Lys Arg Lys Lys Arg Lys Lys Arg Lys
1               5                   10

<210> SEQ ID NO 50
<211> LENGTH: 14
<212> TYPE: PRT
<213> ORGANISM: artificial
<220> FEATURE:
<223> OTHER INFORMATION: synthetic sequence

<400> SEQUENCE: 50

Lys Arg Lys Lys Arg Lys Lys Arg Lys Lys Arg Lys Lys Arg
1               5                   10

<210> SEQ ID NO 51
<211> LENGTH: 16
<212> TYPE: PRT
<213> ORGANISM: artificial
<220> FEATURE:
<223> OTHER INFORMATION: synthetic sequence

<400> SEQUENCE: 51

Lys Lys Lys Lys Lys Lys Lys Lys Lys Lys Lys Lys Lys Lys Lys Lys
1               5                   10                  15

<210> SEQ ID NO 52
<211> LENGTH: 18
<212> TYPE: PRT
<213> ORGANISM: artificial
<220> FEATURE:
<223> OTHER INFORMATION: synthetic sequence

<400> SEQUENCE: 52

Lys Arg Lys Lys Arg Lys Lys Arg Lys Lys Arg Lys Lys Arg Lys Lys
1               5                   10                  15

Arg Lys

<210> SEQ ID NO 53
<211> LENGTH: 19
<212> TYPE: PRT
<213> ORGANISM: artificial
<220> FEATURE:
<223> OTHER INFORMATION: synthetic sequence

<400> SEQUENCE: 53

Lys Arg Lys Lys Arg Lys Lys Arg Lys Lys Arg Lys Lys Arg Lys Lys
1               5                   10                  15

Arg Lys Lys

<210> SEQ ID NO 54
<211> LENGTH: 19
<212> TYPE: PRT
<213> ORGANISM: artificial
<220> FEATURE:
```

<223> OTHER INFORMATION: synthetic sequence

<400> SEQUENCE: 54

Arg Arg Arg Arg Arg Arg Arg Arg Arg Arg Arg Arg Arg Arg Arg
1               5                   10                  15

Arg Arg Arg

<210> SEQ ID NO 55
<211> LENGTH: 19
<212> TYPE: PRT
<213> ORGANISM: artificial
<220> FEATURE:
<223> OTHER INFORMATION: synthetic sequence

<400> SEQUENCE: 55

Lys Lys Lys Lys Lys Lys Lys Lys Lys Lys Lys Lys Lys Lys Lys
1               5                   10                  15

Lys Lys Lys

<210> SEQ ID NO 56
<211> LENGTH: 20
<212> TYPE: PRT
<213> ORGANISM: artificial
<220> FEATURE:
<223> OTHER INFORMATION: synthetic sequence

<400> SEQUENCE: 56

Lys Arg Lys Lys Arg Lys Lys Arg Lys Arg Ser Lys Arg Lys Lys Arg
1               5                   10                  15

Lys Lys Arg Lys
            20

<210> SEQ ID NO 57
<211> LENGTH: 21
<212> TYPE: PRT
<213> ORGANISM: artificial
<220> FEATURE:
<223> OTHER INFORMATION: synthetic sequence

<400> SEQUENCE: 57

Lys Arg Lys Lys Arg Lys Lys Arg Lys Arg Ser Lys Arg Lys Lys Arg
1               5                   10                  15

Lys Lys Arg Lys Lys
            20

<210> SEQ ID NO 58
<211> LENGTH: 21
<212> TYPE: PRT
<213> ORGANISM: artificial
<220> FEATURE:
<223> OTHER INFORMATION: synthetic sequence

<400> SEQUENCE: 58

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 59
<211> LENGTH: 22
<212> TYPE: PRT
<213> ORGANISM: artificial
<220> FEATURE:
<223> OTHER INFORMATION: synthetic sequence

```
<400> SEQUENCE: 59

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 60
<211> LENGTH: 24
<212> TYPE: PRT
<213> ORGANISM: artificial
<220> FEATURE:
<223> OTHER INFORMATION: synthetic sequence

<400> SEQUENCE: 60

Lys Arg Lys Lys Arg Lys Lys Arg Lys Arg Gly Ser Gly Ser Gly Lys
1               5                   10                  15

Arg Lys Lys Arg Lys Lys Arg Lys
            20

<210> SEQ ID NO 61
<211> LENGTH: 25
<212> TYPE: PRT
<213> ORGANISM: artificial
<220> FEATURE:
<223> OTHER INFORMATION: synthetic sequence

<400> SEQUENCE: 61

Lys Arg Lys Lys Arg Lys Lys Arg Lys Lys Arg Lys Lys Arg Lys Lys
1               5                   10                  15

Arg Lys Lys Arg Lys Lys Arg Lys Lys
            20                  25

<210> SEQ ID NO 62
<211> LENGTH: 31
<212> TYPE: PRT
<213> ORGANISM: artificial
<220> FEATURE:
<223> OTHER INFORMATION: synthetic sequence

<400> SEQUENCE: 62

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30

<210> SEQ ID NO 63
<211> LENGTH: 38
<212> TYPE: PRT
<213> ORGANISM: artificial
<220> FEATURE:
<223> OTHER INFORMATION: synthetic sequence

<400> SEQUENCE: 63

Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
            20                  25                  30

Lys Arg Lys Lys Arg Lys
        35

<210> SEQ ID NO 64
<211> LENGTH: 39
```

<212> TYPE: PRT
<213> ORGANISM: artificial
<220> FEATURE:
<223> OTHER INFORMATION: synthetic sequence

<400> SEQUENCE: 64

Lys Arg Lys Lys Arg Lys Lys Arg Lys Lys Arg Lys Lys Arg Lys Lys
1               5                   10                  15
Arg Lys Lys Arg Lys Lys Arg Lys Lys Arg Lys Lys Arg Lys Lys Arg
                20                  25                  30
Lys Lys Arg Lys Lys Arg Lys
            35

<210> SEQ ID NO 65
<211> LENGTH: 42
<212> TYPE: PRT
<213> ORGANISM: artificial
<220> FEATURE:
<223> OTHER INFORMATION: synthetic sequence

<400> SEQUENCE: 65

Lys Arg Lys Lys Arg Lys Lys Arg Lys Arg Ser Lys Arg Lys Lys Arg
1               5                   10                  15
Lys Lys Arg Lys Arg Ser Lys Arg Lys Lys Arg Lys Lys Arg Lys Arg
                20                  25                  30
Ser Lys Arg Lys Lys Arg Lys Lys Arg Lys
            35                  40

<210> SEQ ID NO 66
<211> LENGTH: 37
<212> TYPE: PRT
<213> ORGANISM: Homo sapiens

<400> SEQUENCE: 66

Leu Leu Gly Asp Phe Phe Arg Lys Ser Lys Glu Lys Ile Gly Lys Glu
1               5                   10                  15
Phe Lys Arg Ile Val Gln Arg Ile Lys Asp Phe Leu Arg Asn Leu Val
                20                  25                  30
Pro Arg Thr Glu Ser
            35

<210> SEQ ID NO 67
<211> LENGTH: 29
<212> TYPE: PRT
<213> ORGANISM: unknown
<220> FEATURE:
<223> OTHER INFORMATION: SMAP-29 sheep

<400> SEQUENCE: 67

Arg Gly Leu Arg Arg Leu Gly Arg Lys Ile Ala His Gly Val Lys Lys
1               5                   10                  15
Tyr Gly Pro Thr Val Leu Arg Ile Ile Arg Ile Ala Gly
                20                  25

<210> SEQ ID NO 68
<211> LENGTH: 13
<212> TYPE: PRT
<213> ORGANISM: unknown
<220> FEATURE:
<223> OTHER INFORMATION: Indolicidine bovine

<400> SEQUENCE: 68

Ile Leu Pro Trp Lys Trp Pro Trp Trp Pro Trp Arg Arg

<210> SEQ ID NO 69
<211> LENGTH: 18
<212> TYPE: PRT
<213> ORGANISM: unknown
<220> FEATURE:
<223> OTHER INFORMATION: Protegrin Porcine

<400> SEQUENCE: 69

Arg Gly Gly Arg Leu Cys Tyr Cys Arg Arg Arg Phe Cys Val Cys Val
1               5                   10                  15

Gly Arg

<210> SEQ ID NO 70
<211> LENGTH: 31
<212> TYPE: PRT
<213> ORGANISM: unknown
<220> FEATURE:
<223> OTHER INFORMATION: Cecropin P1 Mammal (pig)

<400> SEQUENCE: 70

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 71
<211> LENGTH: 23
<212> TYPE: PRT
<213> ORGANISM: unknown
<220> FEATURE:
<223> OTHER INFORMATION: Magainin frog

<400> SEQUENCE: 71

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 72
<211> LENGTH: 25
<212> TYPE: PRT
<213> ORGANISM: unknown
<220> FEATURE:
<223> OTHER INFORMATION: Pleurocidin fish

<400> SEQUENCE: 72

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 73
<211> LENGTH: 36
<212> TYPE: PRT
<213> ORGANISM: Aedes aegypti

<400> SEQUENCE: 73

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
        35

<210> SEQ ID NO 74
<211> LENGTH: 40
<212> TYPE: PRT
<213> ORGANISM: Drosophila melanogaster

<400> SEQUENCE: 74

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly
        35                  40

<210> SEQ ID NO 75
<211> LENGTH: 21
<212> TYPE: PRT
<213> ORGANISM: unknown
<220> FEATURE:
<223> OTHER INFORMATION: Buforin II vertebrate

<400> SEQUENCE: 75

Thr Arg Ser Ser Arg Ala Gly Leu Gln Phe Pro Val Gly Arg Val His
1               5                   10                  15

Arg Leu Leu Arg Lys
            20

<210> SEQ ID NO 76
<211> LENGTH: 39
<212> TYPE: PRT
<213> ORGANISM: unknown
<220> FEATURE:
<223> OTHER INFORMATION: Sarcotoxin IA Fly

<400> SEQUENCE: 76

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

<210> SEQ ID NO 77
<211> LENGTH: 17
<212> TYPE: PRT
<213> ORGANISM: Apis mellifera

<400> SEQUENCE: 77

Ala Asn Arg Pro Val Tyr Ile Pro Pro Pro Arg Pro Pro His Pro Arg
1               5                   10                  15

Leu

<210> SEQ ID NO 78
<211> LENGTH: 24
<212> TYPE: PRT
<213> ORGANISM: unknown
<220> FEATURE:
<223> OTHER INFORMATION: Ascaphine 5 Frog

<400> SEQUENCE: 78

Gly Ile Lys Asp Trp Ile Lys Gly Ala Ala Lys Lys Leu Ile Lys Thr

```
1               5                   10                  15
Val Ala Ser His Ile Ala Asn Gln
            20

<210> SEQ ID NO 79
<211> LENGTH: 22
<212> TYPE: PRT
<213> ORGANISM: unknown
<220> FEATURE:
<223> OTHER INFORMATION: Nigrocine 2 Frog

<400> SEQUENCE: 79

Gly Leu Leu Ser Lys Val Leu Gly Val Gly Lys Lys Val Leu Cys Gly
1               5                   10                  15

Val Ser Gly Leu Val Cys
            20

<210> SEQ ID NO 80
<211> LENGTH: 24
<212> TYPE: PRT
<213> ORGANISM: unknown
<220> FEATURE:
<223> OTHER INFORMATION: Pseudin 1 Rana Frog

<400> SEQUENCE: 80

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 81
<211> LENGTH: 18
<212> TYPE: PRT
<213> ORGANISM: unknown
<220> FEATURE:
<223> OTHER INFORMATION: Ranalexin Frog

<400> SEQUENCE: 81

Phe Leu Gly Gly Leu Ile Val Pro Ala Met Ile Cys Ala Val Thr Lys
1               5                   10                  15

Lys Cys

<210> SEQ ID NO 82
<211> LENGTH: 26
<212> TYPE: PRT
<213> ORGANISM: unknown
<220> FEATURE:
<223> OTHER INFORMATION: Melittin bee

<400> SEQUENCE: 82

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 83
<211> LENGTH: 25
<212> TYPE: PRT
<213> ORGANISM: unknown
<220> FEATURE:
<223> OTHER INFORMATION: Lycotoxin 1 Spider

<400> SEQUENCE: 83

Ile Trp Leu Thr Ala Leu Lys Phe Leu Gly Lys His Ala Ala Lys Lys
```

```
                1               5                   10                  15
Leu Ala Lys Gln Gln Leu Ser Lys Leu
            20                  25

<210> SEQ ID NO 84
<211> LENGTH: 19
<212> TYPE: PRT
<213> ORGANISM: unknown
<220> FEATURE:
<223> OTHER INFORMATION: Parasin 1 Fish

<400> SEQUENCE: 84

Lys Gly Arg Gly Lys Gln Gly Gly Lys Val Arg Ala Lys Ala Lys Thr
1               5                   10                  15

Arg Ser Ser

<210> SEQ ID NO 85
<211> LENGTH: 39
<212> TYPE: PRT
<213> ORGANISM: unknown
<220> FEATURE:
<223> OTHER INFORMATION: Buforin I Toad

<400> SEQUENCE: 85

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 86
<211> LENGTH: 34
<212> TYPE: PRT
<213> ORGANISM: unknown
<220> FEATURE:
<223> OTHER INFORMATION: Dermaseptin 1 Frog

<400> SEQUENCE: 86

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 87
<211> LENGTH: 12
<212> TYPE: PRT
<213> ORGANISM: unknown
<220> FEATURE:
<223> OTHER INFORMATION: Bactenecin 1 Cow

<400> SEQUENCE: 87

Arg Leu Cys Arg Ile Val Val Ile Arg Val Cys Arg
1               5                   10

<210> SEQ ID NO 88
<211> LENGTH: 21
<212> TYPE: PRT
<213> ORGANISM: unknown
<220> FEATURE:
<223> OTHER INFORMATION: Thanatin Insect

<400> SEQUENCE: 88
```

```
Gly Ser Lys Lys Pro Val Pro Ile Ile Tyr Cys Asn Arg Arg Thr Gly
1               5                   10                  15

Lys Cys Gln Arg Met
            20

<210> SEQ ID NO 89
<211> LENGTH: 19
<212> TYPE: PRT
<213> ORGANISM: unknown
<220> FEATURE:
<223> OTHER INFORMATION: Brevinin 1T Rana frogs

<400> SEQUENCE: 89

Val Asn Pro Ile Ile Leu Gly Val Leu Pro Lys Val Cys Leu Ile Thr
1               5                   10                  15

Lys Lys Cys

<210> SEQ ID NO 90
<211> LENGTH: 26
<212> TYPE: PRT
<213> ORGANISM: unknown
<220> FEATURE:
<223> OTHER INFORMATION: Ranateurin 1 Rana frog

<400> SEQUENCE: 90

Ser Met Leu Ser Val Leu Lys Asn Leu Gly Lys Val Gly Leu Gly Phe
1               5                   10                  15

Val Ala Cys Lys Ile Asn Ile Lys Gln Cys
            20                  25

<210> SEQ ID NO 91
<211> LENGTH: 46
<212> TYPE: PRT
<213> ORGANISM: unknown
<220> FEATURE:
<223> OTHER INFORMATION: Esculentin 1 Rana frogs

<400> SEQUENCE: 91

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
                20                  25                  30

Thr Gly Ile Lys Ile Ala Gly Cys Lys Ile Lys Gly Glu Cys
            35                  40                  45

<210> SEQ ID NO 92
<211> LENGTH: 17
<212> TYPE: PRT
<213> ORGANISM: Limulus polyphemus

<400> SEQUENCE: 92

Arg Trp Cys Phe Arg Val Cys Tyr Arg Gly Ile Cys Tyr Arg Lys Cys
1               5                   10                  15

Arg

<210> SEQ ID NO 93
<211> LENGTH: 25
<212> TYPE: PRT
<213> ORGANISM: unknown
<220> FEATURE:
<223> OTHER INFORMATION: Androctonin Scorpion

<400> SEQUENCE: 93
```

Arg Ser Val Cys Arg Gln Ile Lys Ile Cys Arg Arg Gly Gly Cys
1               5                   10                  15

Tyr Tyr Lys Cys Thr Asn Arg Pro Tyr
            20                  25

<210> SEQ ID NO 94
<211> LENGTH: 30
<212> TYPE: PRT
<213> ORGANISM: Homo sapiens

<400> SEQUENCE: 94

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 95
<211> LENGTH: 38
<212> TYPE: PRT
<213> ORGANISM: unknown
<220> FEATURE:
<223> OTHER INFORMATION: beta-defensin cow

<400> SEQUENCE: 95

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
        35

<210> SEQ ID NO 96
<211> LENGTH: 18
<212> TYPE: PRT
<213> ORGANISM: unknown
<220> FEATURE:
<223> OTHER INFORMATION: theta-defensin monkey

<400> SEQUENCE: 96

Gly Phe Cys Arg Cys Leu Cys Arg Arg Gly Val Cys Arg Cys Ile Cys
1               5                   10                  15

Thr Arg

<210> SEQ ID NO 97
<211> LENGTH: 40
<212> TYPE: PRT
<213> ORGANISM: unknown
<220> FEATURE:
<223> OTHER INFORMATION: defensin (sapecin A) insect

<400> SEQUENCE: 97

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Ala Val Cys Val Cys Arg Asn
        35                  40

<210> SEQ ID NO 98
<211> LENGTH: 46
<212> TYPE: PRT
<213> ORGANISM: unknown

```
<220> FEATURE:
<223> OTHER INFORMATION: Thionin (crambin) plant

<400> SEQUENCE: 98

Thr Thr Cys Cys Pro Ser Ile Val Ala Arg Ser Asn Phe Asn Val Cys
1               5                   10                  15

Arg Ile Pro Gly Thr Pro Glu Ala Ile Cys Ala Thr Tyr Thr Gly Cys
            20                  25                  30

Ile Ile Ile Pro Gly Ala Thr Cys Pro Gly Asp Tyr Ala Asn
            35                  40                  45

<210> SEQ ID NO 99
<211> LENGTH: 50
<212> TYPE: PRT
<213> ORGANISM: unknown
<220> FEATURE:
<223> OTHER INFORMATION: defensin from radish

<400> SEQUENCE: 99

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Cys Ile Cys Tyr Phe
        35                  40                  45

Pro Cys
    50

<210> SEQ ID NO 100
<211> LENGTH: 44
<212> TYPE: PRT
<213> ORGANISM: Drosophila melanogaster

<400> SEQUENCE: 100

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
            20                  25                  30

Cys Ser Pro Ser Leu Lys Cys Trp Cys Glu Gly Cys
        35                  40

<210> SEQ ID NO 101
<211> LENGTH: 25
<212> TYPE: PRT
<213> ORGANISM: Homo sapiens

<400> SEQUENCE: 101

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 102
<211> LENGTH: 44
<212> TYPE: PRT
<213> ORGANISM: unknown
<220> FEATURE:
<223> OTHER INFORMATION: Bac 5 Cow

<400> SEQUENCE: 102

Arg Phe Arg Pro Pro Ile Arg Arg Pro Pro Ile Arg Pro Pro Phe Tyr
1               5                   10                  15
```

```
Pro Pro Phe Arg Pro Pro Ile Arg Pro Ile Phe Pro Pro Ile Arg
            20                  25                  30

Pro Pro Phe Arg Pro Pro Leu Gly Arg Pro Phe Pro
            35                  40
```

<210> SEQ ID NO 103
<211> LENGTH: 39
<212> TYPE: PRT
<213> ORGANISM: unknown
<220> FEATURE:
<223> OTHER INFORMATION: PR-39 Pig

<400> SEQUENCE: 103

```
Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
            35
```

<210> SEQ ID NO 104
<211> LENGTH: 20
<212> TYPE: PRT
<213> ORGANISM: unknown
<220> FEATURE:
<223> OTHER INFORMATION: Pyrrhocoricin Insect

<400> SEQUENCE: 104

```
Val Asp Lys Gly Ser Tyr Leu Pro Arg Pro Thr Pro Pro Arg Pro Ile
1               5                   10                  15

Tyr Asn Arg Asn
            20
```

<210> SEQ ID NO 105
<211> LENGTH: 24
<212> TYPE: PRT
<213> ORGANISM: Homo sapiens

<400> SEQUENCE: 105

```
Asp Ser His Ala Lys Arg His His Gly Tyr Lys Arg Lys Phe His Glu
1               5                   10                  15

Lys His His Ser His Arg Gly Tyr
            20
```

<210> SEQ ID NO 106
<211> LENGTH: 19
<212> TYPE: PRT
<213> ORGANISM: Unknown
<220> FEATURE:
<223> OTHER INFORMATION: ECP19

<400> SEQUENCE: 106

```
Arg Pro Pro Gln Phe Thr Arg Ala Gln Trp Phe Ala Ile Gln His Ile
1               5                   10                  15

Ser Leu Asn
```

<210> SEQ ID NO 107
<211> LENGTH: 23
<212> TYPE: PRT
<213> ORGANISM: Unknown
<220> FEATURE:
<223> OTHER INFORMATION: MSI-594

-continued

```
<400> SEQUENCE: 107

Gly Ile Gly Lys Phe Leu Lys Lys Ala Lys Lys Gly Ile Gly Ala Val
1               5                   10                  15

Leu Lys Val Leu Thr Thr Gly
            20

<210> SEQ ID NO 108
<211> LENGTH: 35
<212> TYPE: PRT
<213> ORGANISM: Unknown
<220> FEATURE:
<223> OTHER INFORMATION: TL-ColM

<400> SEQUENCE: 108

Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro
        35

<210> SEQ ID NO 109
<211> LENGTH: 18
<212> TYPE: PRT
<213> ORGANISM: Unknown
<220> FEATURE:
<223> OTHER INFORMATION: SBO

<400> SEQUENCE: 109

Lys Leu Lys Lys Ile Ala Gln Lys Ile Lys Asn Phe Phe Ala Lys Leu
1               5                   10                  15

Val Ala

<210> SEQ ID NO 110
<211> LENGTH: 34
<212> TYPE: PRT
<213> ORGANISM: Limulus polyphemus

<400> SEQUENCE: 110

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser

<210> SEQ ID NO 111
<211> LENGTH: 18
<212> TYPE: PRT
<213> ORGANISM: artificial
<220> FEATURE:
<223> OTHER INFORMATION: synthetic sequence

<400> SEQUENCE: 111

Gly Phe Phe Ile Pro Ala Val Ile Leu Pro Ser Ile Ala Phe Leu Ile
1               5                   10                  15

Val Pro

<210> SEQ ID NO 112
<211> LENGTH: 5
<212> TYPE: PRT
<213> ORGANISM: artificial
<220> FEATURE:
```

<223> OTHER INFORMATION: synthetic sequence

<400> SEQUENCE: 112

Phe Phe Val Ala Pro
1               5

<210> SEQ ID NO 113
<211> LENGTH: 13
<212> TYPE: PRT
<213> ORGANISM: unknown
<220> FEATURE:
<223> OTHER INFORMATION: alpha4-helix of T4 lysozyme

<400> SEQUENCE: 113

Pro Asn Arg Ala Lys Arg Val Ile Thr Thr Phe Arg Thr
1               5                   10

<210> SEQ ID NO 114
<211> LENGTH: 27
<212> TYPE: PRT
<213> ORGANISM: artificial
<220> FEATURE:
<223> OTHER INFORMATION: synthetic sequence

<400> SEQUENCE: 114

Lys Arg Trp Val Lys Arg Val Lys Arg Val Lys Arg Trp Val Lys Arg
1               5                   10                  15

Val Val Arg Val Val Lys Arg Trp Val Lys Arg
            20                  25

<210> SEQ ID NO 115
<211> LENGTH: 25
<212> TYPE: PRT
<213> ORGANISM: Artificial Sequence
<220> FEATURE:
<223> OTHER INFORMATION: synthetic sequence; MW2

<400> SEQUENCE: 115

Gly Lys Pro Gly Trp Leu Ile Lys Val Ala Leu Lys Phe Lys Lys Leu
1               5                   10                  15

Ile Arg Arg Pro Leu Lys Arg Leu Ala
            20                  25

<210> SEQ ID NO 116
<211> LENGTH: 261
<212> TYPE: PRT
<213> ORGANISM: Artificial sequence
<220> FEATURE:
<223> OTHER INFORMATION: Fusion of SMAP-29, CBD of KZ144 endolysin
      (three cysteines replaced by serine, K59M) with LYS68 endolysin
      (P78S)

<400> SEQUENCE: 116

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Ser Gln Leu Gln
        35                  40                  45

Thr Leu Leu Asn Leu Ser Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

-continued

```
Ser Leu Asp Ser Asp Gly Ile Val Gly Met Asn Thr Trp Ala Glu Leu
                85                  90                  95
Phe Ser Lys Tyr Ser Asn Arg Asn Ile Ser Asp Asn Gly Ile Lys Phe
            100                 105                 110
Thr Ala Ala Phe Glu Gly Phe Arg Gly Thr Ala Tyr Arg Ala Thr Lys
        115                 120                 125
Asn Glu Lys Tyr Leu Thr Ile Gly Tyr Gly His Tyr Gly Ala Asp Val
    130                 135                 140
Lys Glu Gly Gln Lys Ile Thr Glu Gly Gln Gly Leu Leu Leu Leu His
145                 150                 155                 160
Lys Asp Met Val Lys Ala Val Ala Ala Val Asp Ala Val Ala His Pro
                165                 170                 175
Ser Leu Asn Gln Ser Gln Phe Asp Ala Met Cys Asp Leu Val Tyr Asn
            180                 185                 190
Ala Gly Val Gly Val Ile Ala Ala Ser Thr Gly Thr Gly Gln Ala Leu
        195                 200                 205
Arg Lys Gly Asp Val Ala Thr Leu Arg Asn Lys Leu Thr Gln Phe His
    210                 215                 220
Tyr Gln Asn Gly Lys Ser Leu Leu Gly Leu Arg Arg Arg Ala Ala Gly
225                 230                 235                 240
Arg Val Ala Leu Phe Asp Gly Met Leu Trp Gln Gln Ala Glu Ala Ile
                245                 250                 255
Gly Arg Gly Ala Lys
            260

<210> SEQ ID NO 117
<211> LENGTH: 4
<212> TYPE: PRT
<213> ORGANISM: artificial
<220> FEATURE:
<223> OTHER INFORMATION: linker

<400> SEQUENCE: 117

Gly Ala Gly Ala
1

<210> SEQ ID NO 118
<211> LENGTH: 8
<212> TYPE: PRT
<213> ORGANISM: artificial
<220> FEATURE:
<223> OTHER INFORMATION: linker

<400> SEQUENCE: 118

Gly Ala Gly Ala Gly Ala Gly Ala
1               5

<210> SEQ ID NO 119
<211> LENGTH: 12
<212> TYPE: PRT
<213> ORGANISM: artificial
<220> FEATURE:
<223> OTHER INFORMATION: linker

<400> SEQUENCE: 119

Gly Ala Gly Ala Gly Ala Gly Ala Gly Ala Gly Ala
1               5                   10

<210> SEQ ID NO 120
<211> LENGTH: 6
<212> TYPE: PRT
```

```
<213> ORGANISM: artificial sequence
<220> FEATURE:
<223> OTHER INFORMATION: His-Tag (6x)

<400> SEQUENCE: 120

His His His His His His
1               5
```